United States Patent [19]

Amstutz et al.

[11] Patent Number: 5,795,864
[45] Date of Patent: Aug. 18, 1998

[54] STABLE OMEGA CONOPETIDE FORMULATIONS

[75] Inventors: Gary Arthur Amstutz, San Jose; Stephen Scott Bowersox, Menlo Park; Kishorchandra Gohil, Richmond; Peter Isadore Adriaenssens, Mountain View; Ramasharma Kristipati, Fremont, all of Calif.

[73] Assignee: Neurex Corporation, Menlo Park, Calif.

[21] Appl. No.: 496,847

[22] Filed: Jun. 27, 1995

[51] Int. Cl.⁶ ............................ A61K 38/00; C07K 5/00; C07K 7/00

[52] U.S. Cl. ................................. 514/12; 530/324
[58] Field of Search ..................... 530/324; 514/12

[56] References Cited

U.S. PATENT DOCUMENTS 5,587,454  12/1996  Justice et al. ................. 530/324

Primary Examiner—Avis M. Davenport
Attorney, Agent, or Firm—Peter J. Dehlinger; Carol A. Stratford

[57] ABSTRACT

Disclosed are formulations effective to stabilize omega conotoxin peptide preparations at elevated temperatures. Novel omega conopeptides also form part of the invention.

7 Claims, 12 Drawing Sheets

|  | 1 | 5 | 10 | 15 | 20 | 25 | 30 |
|---|---|---|---|---|---|---|---|
| MVIIA/SNX-111 | C K G K G A K C S R L M Y D C C T G S C — R — S G K — C | | | | | | |
| MVIIB/SNX-159 | C K G K G A S C H R T S Y D C C T G S C N R — — G K — C | | | | | | |
| GVIA/SNX-124 | C K S X G S S C S X T S Y N C C R — S C N X Y T — K R C — Y | | | | | | |
| GVIIB/SNX-178 | C K S X G T X C S R G M R D C C T — S C L L Y S N K — C R R Y | | | | | | |
| RVIA/SNX-182 | C K P X G S X C R V S S Y N C C S — S C K S Y — N K K C G | | | | | | |

Fig. 1A

|  | 1 | | | | 5 | | | | | 10 | | | | | 15 | | | | | 20 | | | | | 25 | | | | | 30 |
|---|---|---|---|---|---|---|---|---|---|---|---|---|---|---|---|---|---|---|---|---|---|---|---|---|---|---|---|---|---|---|
| SVIA/SNX-157 | C | R | S | S | G | S | X | C | G | V | T | S | I | – | C | C | – | G | R | C | – | – | Y | R | G | K | – | C | T |
| TVIA/SNX-185 | C | L | S | X | G | S | S | C | S | X | T | S | Y | N | C | C | R | – | S | C | N | X | Y | S | – | R | K | C | R |
| SVIB/SNX-183 | C | K | L | K | G | Q | S | C | R | K | T | S | Y | D | C | C | S | G | S | C | G | R | – | S | G | K | – | C |  |
| MVIIC/SNX-230 | C | K | G | K | G | A | P | C | R | K | T | M | Y | D | C | C | S | G | S | C | G | R | – | R | G | K | – | C |  |
| SNX-231 | C | K | G | K | G | A | X | C | R | K | T | M | Y | D | C | C | S | G | S | C | G | R | – | R | G | K | – | C |  |

Fig. 1B

| | 1 | | | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|---|---|
| MVIIA (SNX-111) | C | K | G | K | G | A | K | C | S | R | L | M | Y | D | C | C | T | G | S | C | R | S | G | K | C | -NH$_2$ |
| SNX-190 | - | - | - | - | - | A | - | - | - | - | - | - | - | - | - | - | - | - | - | - | - | - | - | - | - | NH$_2$ |
| SNX-191 | - | - | A | - | - | - | - | - | - | - | - | - | - | - | - | - | - | - | - | - | - | - | - | - | - | NH$_2$ |
| SNX-193 | - | - | - | - | - | - | - | - | - | - | - | - | - | - | - | - | - | - | - | - | - | - | - | - | - | G-OH |
| SNX-194 | - | - | - | - | - | - | - | - | - | - | - | -Nle- | - | - | - | - | - | - | - | - | - | - | - | - | - | NH$_2$ |
| SNX-195 | - | - | - | - | - | - | - | - | - | - | - | - | - | - | - | - | - | - | - | - | - | - | - | A | - | NH$_2$ |
| SNX-196 N- | - | - | - | - | - | - | - | - | - | - | - | - | - | - | - | - | - | - | - | - | - | - | - | - | - | G-OH |
| SNX-197 NS- | - | - | - | - | - | - | - | - | - | - | - | - | - | - | - | - | - | - | - | - | - | - | - | - | - | NH$_2$ |
| SNX-198 | - | - | - | - | - | - | - | - | - | - | - | - | - | - | - | - | - | - | - | - | - | A | - | - | - | NH$_2$ |
| SNX-199 | - | - | - | - | - | - | - | - | - | A | - | - | - | - | - | - | - | - | - | - | - | - | - | - | - | NH$_2$ |

Fig. 2A

|  | 1 | 5 | 10 | 15 | 20 | 25 |  |
|---|---|---|---|---|---|---|---|
| SNX-200 | - - - - | - A - - | - - - - | - - - - | - - - - | - - - - | NH₂ |
| SNX-201 | - - - - | - - - - | R K T S | - - - - | - - - - | - - - - | NH₂ |
| SNX-239 | - - - - | - - - - | - - L - | - - - - | - - - - | - - - - | NH₂ |
| SNX-240 Ac- | - - - - | - - - - | - - L - | - - - - | - - - - | - - - - | NH₂ |
| SVIB (SNX-183) | C K L K | G Q S C | R K T S | Y D C C | S G S C | G R S G K C | NH₂ |
| SNX-202 | - - - - | - - - - | S R L M | - - - - | | | NH₂ |
| TVIA (SNX-185) | C L S X | G S S C | S X T S | Y N C C | R S C N | X Y S R K C R | NH₂ |
| SNX-207 | - - - - | - - - - | - R L M | - - - - | | | NH₂ |
| SNX-236 | - - - - | - - - - | - R L M | - - - P | | | NH₂ |

```
             1         5         10        15        20        25        30
I.
MVIIA    C K G K G A K C S R L M Y D C C T G S C - R - S G K - C
MVIIB    C K G K G A S C H R T S Y D C C T G S C N R - I - G K - C

II.
TVIA     C L S X G S S C S X T S Y N C C R - S C N X Y S R K - C R
SNX-207  C L S X G S S C S R L M Y N C C R - S C N X Y S R K - C R

III.
RVIA     C K P X G S X C R V S S Y N C C S - S C K S Y - N K K C G
SVIA     C R S S G S X C R S G V T S I - C C - G R C - Y R G K C T
GVIIA    C K S X G T X C S R G M R D C C T - S C L L Y S N K C R R Y D
SVIB     C K L K G Q S C R K T S Y D C C S G S C G R - S G K - C
MVIIC    C K G K G A P C R K T M Y D C C S G S C G R - R G K - C
SNX-231  C K G K G A X C R K T M Y D C C S G S C G R - R G K - C
```

1

STABLE OMEGA CONOPETIDE FORMULATIONS

FIELD OF THE INVENTION

The present invention relates to methods of preventing progression of neuropathic pain and to formulations suitable for stabilizing omega conopeptide peptides used in such treatment methods.

REFERENCES

Ahmad, S. N. and Miljanich, G. P., *Brain Research* 453:247–256 (1988).

Bennett, G. J. and Xie, Y.-K., *Pain* 33:87–107 (1988).

Bennett, J. P. et al., in *NEUROTRANSMITTER RECEPTOR BINDING*, pp. 61–89; Raven Press, New York, N.Y. (1983).

Ben-Sreti, M. M., et al., *Eur. J. Pharmacol.* 90:385–391 (1983).

Contreras, E., et al., *Eur. J. Pharmacol.* 148:463–466 (1988).

Dixon, W. J., *Ann. Rev. Pharmacol. Toxicol.* 20:441–462 (1976).

Gray, W., et al., *Annual Review of Biochemistry* 57:665–700 (1988).

Jadad, A. R., et al., *Lancet* 339:1367–1371 (1992).

Kenakin, T. P., in *PHARMACOLOGIC ANALYSIS OF DRUG RECEPTOR INTERACTION*, Raven Press, New York, N.Y. (1987).

Kim, S. H. and Chung, J. M., *Pain* 50:355–363 (1992).

McCleskey, E. W., et al., *Proc. Natl. Acad. Sci. USA* 84:4327–31 (1987).

McGeer, P. L., et al., in *MOLECULAR NEUROBIOLOGY OF THE MAMMALIAN BRAIN*, Plenum Press, New York, N.Y. (1987).

Nowycky, M. C., et al., *Nature* (London) 316:440–443 (1985).

Olivera, B., et al., *Biochemistry* 23:5087–5090 (1984).

Sher, E. et al., *FASEB J.* 5:2677–2683 (1991).

Sher, E. and Clementi, F., *Neuroscience* 42301–42307 (1991).

Yaksh, T. L., and Rudy, T. A., *Physiol. Behav.* 17:1031–1036 (1976).

Yamashiro, D., *Int. J. Peptide Protein Res.* 30:9–12 (1987).

BACKGROUND OF THE INVENTION

Chronic or intractable pain, as may occur in conditions such as bone degenerative diseases, AIDS, Reflex sympathetic dystrophy (RSD), and cancer, is a debilitating condition which is treated with a variety of analgesic agents, and often opioid compounds, such as morphine.

Neuropathic pain is a particular type of pain that has a complex and variable etiology. It is frequently a chronic condition attributable to complete or partial transection of a nerve, trauma or injury to a nerve, nerve plexus or soft tissue, or other conditions, including cancer, AIDS and idiopathic causes. Neuropathic pain is characterized by hyperalgesia (lowered pain threshold and enhanced pain perception) and by allodynia (pain from innocuous mechanical or thermal stimuli). The condition is progressive in nature. Because the hyperesthetic component of neuropathic pain does not respond to the same pharmaceutical interventions as does more generalized and acute forms of pain, development of effective longterm treatment modalities has been problematic.

Opioid compounds (opiates) such as morphine, while effective in producing analgesia for many types of pain, are generally not effective for treating the progressive stages of neuropathic pain. Moreover, these compounds are known to induce tolerance in patients, so that increased doses are required to achieve a satisfactory analgesic effect. At high doses, these compounds produce side effects, such as respiratory depression, which can be life threatening. In addition, opioids can produce physical dependence in patients. Dependence appears to be related to the dose of opioid taken and the period of time over which it is taken by the subject. For this reason, alternate therapies for the management of chronic pain are widely sought after. In addition, compounds which serve as either a replacement for or as an adjunct to opioid treatment in order to decrease the dosage of analgesic compound required, have utility in the treatment of pain, particularly pain of the chronic, intractable type.

Although calcium blocking agents, including a number of L-type calcium channel antagonists, have been tested as adjunct therapy to morphine analgesia, positive results are attributed to direct effects on calcium availability, since calcium itself is known to attenuate the analgesic effects of certain opioid compounds (Ben-Sreti, et al., 1983). EGTA, a calcium chelating agent, is effective in increasing the analgesic effects of opioids. However, results from tests of calcium antagonists as adjunct therapy to opioids have been contradictory; some L-type calcium channel antagonists have been shown to increase the analgesic effects of opioids, while others of these compounds have been shown to decrease opioid effects (Contreras, et al., 1988).

U.S. Pat. No. 5,051,403 describes the use of omega-conopeptides having defined binding/inhibitory properties in the treatment of ischemia-related neuronal damage. U.S. Pat. No. 5,364,842 demonstrates the effectiveness of omega-conopeptide compositions in certain animal models of pain. Specifically, omega-conopeptides MVIIA and TVIA and derivatives thereof having related inhibitory and binding activities were demonstrated to produce analgesia in animal models of analgesia in which morphine is the standard positive control. Co-owned application U.S. Ser. No. 08/049,794 discloses that omega conopeptides also exhibit analgesic properties in certain models of analgesia, such as neuropathic pain models of analgesia, in which morphine is not expected to produce positive results.

The present invention is based on the discovery that N-type voltage-sensitive calcium channel (VSCC) blocking compounds, including omega conopeptides, are effective to prevent progression of neuropathic conditions. Also disclosed are improved routes of administration for providing relief from neuropathic pain. In addition, the present invention discloses stabilized conopeptide formulations that are particularly useful in the treatment methods of the present invention. These stabilized compositions also find use in other applications in which prolonged administration or long-term storage of solutions containing conopeptides are required.

SUMMARY OF THE INVENTION

In one aspect, the invention includes a method of preventing progression of neuropathic pain. According to the method, the subject is given an N-type voltage-sensitive sensitive calcium channel blocking compound which is effective (a) to inhibit electrically stimulated contraction of the guinea pig ileum, and (b) to bind selectively to omega conopeptide MVIIA binding sites present in neuronal tissue. In a specific embodiment, the activities of the compound in inhibiting the guinea pig ileum and in binding to the MVIIA binding site are within the ranges of such activities of omega-conotoxins MVIIA and TVIA. In another embodiment of the invention, the neuropathic pain is characterized by nociceptor sensitization.

In a more specific embodiment, the activity of the compound to bind selectively to the omega conopeptide MVIIA binding sites is measured by a selectivity ratio of binding at the MVIIA binding site to binding at a site 2 omega conopeptide binding site. Effective compounds will have a selectivity ratio which is within the range of selectivity ratios determined for omega conopeptides MVIIA/SNX-111, SNX-199, SNX-236, SNX-239 and TVIA/SNX-185.

In a preferred embodiment, the N-type calcium channel blocking compounds are omega-conopeptides. In another preferred embodiment, the omega conopeptide is selected from the group consisting of SEQ ID NO: 7 (TVIA/SNX-185), SEQ ID NO:1 (MVIIA/SNX-111), SEQ ID NO: 30 (SNX-236), SEQ ID NO: 2 (SNX-159), SEQ ID NO: 32 (SNX-239), SEQ ID NO: 33 (SNX-199), SEQ ID NO: 35 (SNX273), SEQ ID NO: 36 (SNX-279), and derivatives thereof.

Such peptides may preferably be administered by transdermal iontophoresis. In another preferred embodiment, the conopeptide formulation will include an anti-oxidant effective to prevent methionine oxidation.

In other preferred embodiments, the method of the invention will include administering compound by means effective to deliver compound to regions of neuropathic pain. In one preferred embodiment, the compound is administered by perineural application of compound. In another preferred embodiment, such administering is by topical application to a skin region characterized by proliferation of neurite outgrowth. Such topical administration may further include use of a transdermal patch. In another embodiment, the compound is administered by subdermal injection in a region characterized by proliferation of neurite outgrowth.

In yet another embodiment, the compound is administered by epidural injection. When practicing this method of the invention using an omega conopeptide compound, the treatment method may include means for enhancing permeation of the conopeptide through meningeal membranes. Such membrane permeation enhancing means can include, for example, liposomal encapsulation of the peptide, addition of a surfactant to the composition, or addition of an ion-pairing agent. Also encompassed by the invention is a membrane permeability enhancing means that includes administering to the subject a hypertonic dosing solution effective to disrupt meningeal barriers.

In another aspect, the invention includes a stable omega conopeptide formulation. This formulation includes, in addition to an omega conopeptide, an anti-oxidant capable of preventing methionine oxidation. In one embodiment, the anti-oxidative composition includes a carboxylic acid buffer. Generally, the buffer pH will be below about pH 6, and in a preferred embodiment, the carboxylic acid buffer is lactate buffer adjusted to a pH of about 4–4.5.

In another embodiment, the formulation includes methionine as an anti-oxidant. Generally, the formulation will be in a range below about pH 6. In a more specific embodiment, the methionine formulation buffer includes 0.9% sodium chloride acidified to a pH of about 4–4.5. The foregoing specific lactate and methionine formulations may be used alone or in combination with each other or with other anti-oxidant or stabilizing solutions known in the art. Although such anti-oxidant formulations can be used with any omega-conopeptide that is susceptible to oxidation, they are particularly useful for conopeptides SNX-111, SNX-178, SNX 207, and SNX-236.

The invention further includes, in a related embodiment a method of stabilizing an omega conopeptide solution. The method includes adding to an omega conopeptide-containing solution an anti-oxidant composition capable of preventing methionine oxidation, as described above.

In still a further aspect, the invention includes omega-conopeptide SNX-273 having the sequence: SEQ ID NO: 35. In another aspect, the invention includes omega conopeptide SNX-279 having the sequence SEQ ID NO: 36.

BRIEF DESCRIPTION OF THE DRAWINGS

FIGS. 1A and 1B show primary sequences of several natural omega-conopeptides, MVIIA/SNX-111 (SEQ ID NO:01), MVIIB/SNX-159 (SEQ ID NO: 02), GVIA/SNX-124 (SEQ ID NO: 03), GVIIA/SNX-178 (SEQ ID NO: 04), RVIA/SNX-182 (SEQ ID NO: 05), SVIA/SNX-157 (SEQ ID NO: 06), TVIA/SNX-185 (SEQ ID NO: 07), SVIB/SNX-183 (SEQ ID NO: 08), and MVIIC/SNX-230 (SEQ ID NO: 29), and SNX-231 (SEQ ID NO: 21);

FIGS. 2A and 2B show primary sequences of analog omega-conopeptides SNX-190 (SEQ ID NO: 09), SNX-191 (SEQ ID NO: 10), SNX-193 (SEQ ID NO: 11), SNX-194 (SEQ ID NO: 12), SNX-195 (SEQ ID NO: 13), SNX-196 (SEQ ID NO: 14), SNX-197 (SEQ ID NO: 15), SNX-198 (SEQ ID NO: 16), SNX-199 (SEQ ID NO: 33), SNX-200 (SEQ ID NO: 17), SNX-201 (SEQ ID NO: 18), SNX-239 (SEQ ID NO: 32), SNX240 (SEQ ID NO: 34), SNX-202 (SEQ ID NO: 19), SNX-207 (SEQ ID NO: 20), SNX-236 (SEQ ID NO: 30), SNX-273 ([ala$^{12}$-SNX-111; SEQ ID NO: 35), and SNX-279 (Met(0)$^{12}$-SNX-111; SEQ ID NO: 36) and their relationships to SNX-111 (SEQ ID NO: 01), SNX-185 (SEQ ID NO: 07) or SNX-183 (SEQ ID NO: 08), where Nle indicates norleucine, and Met(0) indicates a sulfoxy-methionine substitution;

FIG. 5 shows omega-conopeptide groupings: I. MVIIA, SNX-199 (SEQ ID NO: 33), MVIIB and SNX-239 (SEQ ID NO: 32), II. TVIA, SNX-207 and SNX-236, III. RVIA, SVIA, GVIIA, SVIB, MVIIC, SNX-231;

DETAILED DESCRIPTION OF THE INVENTION

Figure 3A:
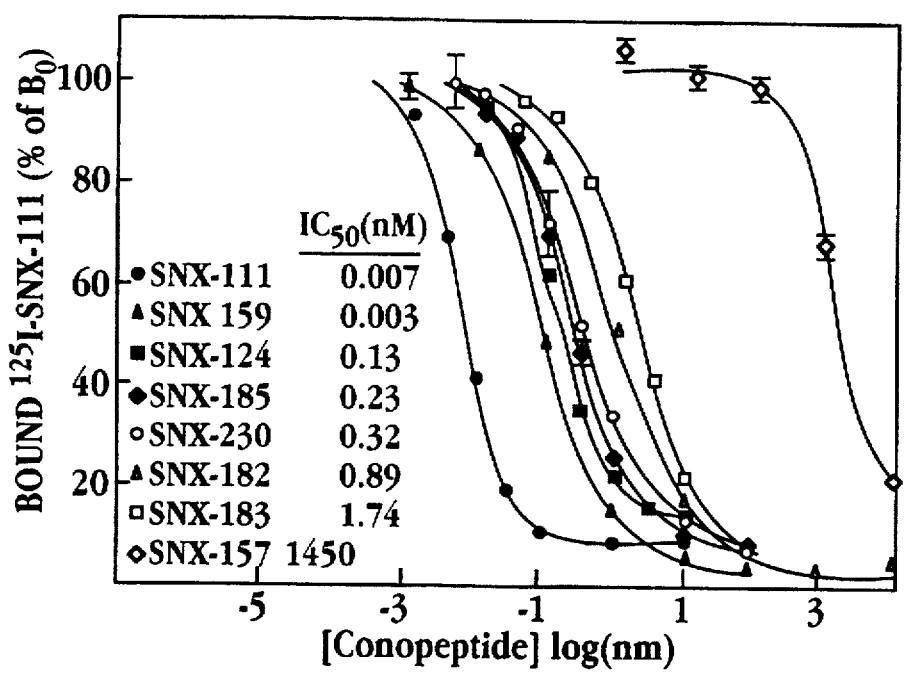
FIGS. 3A and 3B show computer-fit competitive binding curves for omega-conopeptide binding to the OCT MVIIA (SNX-111) binding site in rat brain synaptosomes.

I. N-type Voltage-Sensitive Calcium Channel Blocking Compounds

Voltage-gated calcium channels are present in neurons, and in cardiac, smooth, and skeletal muscle and other excitable cells. These channels are known to be involved in membrane excitability, muscle contraction, and cellular secretion, such as in exocytotic synaptic transmission (McCleskey, et al., 1987). In neuronal cells, voltage-gated calcium channels have been classified by their electrophysiological as well as by their biochemical (binding) properties.

Calcium channels are generally classified according to their electrophysiological properties as Low-voltage-activated (LVA) or High-voltage-activated (HVA) channels. HVA channels are currently known to comprise at least three groups of channels, known as L-, N- and P-type channels (Nowycky, et al., 1985; Sher, et al., 1991). These channels have been distinguished one from another structurally and electrophysiologically as well as biochemically on the basis of their pharmacology and ligand binding properties. Thus, dihydropyridines, diphenylalkylamines and piperidines bind to the alpha, subunit of the L-type calcium channel and block a proportion of HVA calcium currents in neuronal tissue, which are termed L-type calcium currents.

N- or omega- type HVA calcium channels are distinguishable from other calcium channels by their sensitivity to omega conotoxins (omega conopeptides). Such channels are insensitive to dihydropyridine compounds, such as L-type calcium channel blockers nimodipine and nifedipine (Sher, et al., 1991; Sher and Clementi, 1991).

A. Omega-Conopeptides Omega-conopeptides are components of peptide toxins produced by marine snails of the genus Conus, and which act as calcium channel blockers (Gray, et al., 1988). About 500 species of cone snails in the Conus genus have been identified, and a variety of omega-conopeptides from several of these species have been isolated. The primary sequences of eight naturally-occurring omega-conopeptides are shown in FIG. 1, where SNX-231 is an alternative form of MVIIC/SNX-230. Conventional letter initials are used for the amino acid residues, and X represents 4-hydroxyproline, also abbreviated 4Hyp. All of the peptides shown in the figure are amidated at their C-termini.

The peptides shown in FIG. 1 are identified by names which are commonly associated with either the naturally occurring peptide (single letter followed by a Roman numeral followed by a single letter), and by a synthetic designation (SNX-plus numeral). Either or both of these designations will be used interchangeably throughout the specification. For example, the peptide whose sequence is designated MVIIA/SNX-111 will be referred to herein as OCT MVIIA, or alternatively, SNX-111, the latter to signify that the compound is synthetic in origin. Synthetic and naturally occurring peptides having the same sequence behave substantially identically in the assays and methods of treatment of the invention. The OCT MVIIA (SNX-111) and OCT GVIA (SNX-124) peptides also have the common names CmTx and CgTx, respectively. All of the omega-conopeptides have three disulfide linkages connecting cysteine residues 1 and 4, 2 and 5, and 3 and 6, as indicated for the MVIIA peptide in FIG. 2A. FIGS. 2A and 2B shows analogs or derivatives of natural OCT MVIIA, OCT TVIA, and OCT SVIB peptides which have been synthesized and tested in accordance with the invention. Standard single amino acid code letters are used in the figure; X=hydroxyproline; Nle=norleucine; Met(O)=sulfoxymethionine; $NH_2$ group at the C terminus indicates that the peptide is C-terminal amidated; G—OH indicates termination in an unmodified glycine residue.

B. Preparation of Omega Conopeptides

This section describes the synthesis, by solid phase methods, of several naturally occurring omega conotoxin (OCT) peptides and additional omega-conopeptides which are used in the present invention.

Omega-conopeptides, such as those shown in FIGS. 1 and 2, can be synthesized by conventional solid phase methods, such as have been described (Olivera, et al., 1984). Briefly, N-alpha-protected amino acid anhydrides are prepared in crystallized form or prepared freshly in solution and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1–2 reaction cycles are used for the first twelve residue additions, and 2–3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the resin. After removal of the hydrogen fluoride, the peptide is extracted into 1M acetic acid solution and lyophilized. The three disulfide linkages in the peptides may be formed by air oxidation in the presence of dithiothreitol (DTT) or optionally other thiol containing compounds (e.g., cysteine, glutathione), according to procedures detailed in Example 1.

The peptide can be isolated by an initial separation by gel filtration, to remove peptide dimers and higher molecular weight polymers, and also to remove undesired salts, such as guanidine hydrochloride, used in the oxidation reaction. The partially purified peptide is further purified by preparative HPLC chromatography, and the purity and identity of the peptide confirmed by amino acid composition analysis, mass spectrometry and by analytical HPLC in two different solvent systems.

C. Stable Omega-conopeptide Formulations

Dilute solutions of omega-conopeptides are generally unstable in solution, as evidenced by oxidation of methionine residues and reduction or loss of biological activity. In accordance with an important aspect of the present invention, it has been discovered that omega-conopeptides can be significantly stabilized in solution by preventing oxidation of methionine residues present in the peptide structure. In particular, SNX-111, which contains a methionine at position 12, is approximately 10-fold less potent in binding to omega-conopeptide MVIIA binding sites, when its methionine is present in the sulfoxy form.

In experiments carried out in support of the present invention, it has been found that SNX-111 oxidation can be prevented by addition of lactate buffer to the composition. More particularly buffers containing 150 mM lactate buffer, pH 4–4.5 improve stability of the compound considerably. It is known that solutions of SNX-111 in which the peptide concentration is less than about 0.1 mg/ml oxidize rapidly when dissolved in water, saline, or any of a number of buffers used in the art of peptide chemistry. It is a discovery of the present invention that solutions of SNX-111 ranging from 0.01–0.1 mg/ml are stable at 45° C. for weeks, when stabilized with lactate (150 mM, pH 4–4.5). In addition, buffers containing 50 µg/ml methionine are also effective in stabilizing SNX-111. Here, either 150 mM lactate buffer or acidified saline (pH 4–4.5) can be used to buffer the solution.

The foregoing stabilization method and formulation will find particular use in preventing oxidation of those compounds containing methionine residues. With reference to FIGS. 1 and 2, such compounds include SNX-111, SNX-178, SNX-190, SNX-191, SNX-193, SNX-194, SNX-197, SNX-198, SNX-199, SNX-200, SNX-202, SNX-207, SNX-236, SNX-237, SNX-239, SNX-240; however, it is appreciated that the formulation buffer conditions may be used with peptides that lack methionine, as well.

Formulations which incorporate the components or principles discussed above may be used in a number of pharmaceutical applications related to omega conopeptide administration. Solutions of peptides provided in vials may be stored under the acidic formulation conditions, prior to dilution into a pharmaceutical excipient suitable for parenteral administration. Solutions used for slow infusion may also be preserved in this manner. The solution may be administered directly or neutralized prior to administration, according to the particular route of administration in which the formulation is used. For example, direct intrathecal administration of approximately 10 μl of SNX-111 in lactate buffer (150 mM, pH 4–4.5) has been used in treating rats, without noticeable untoward effects. For administration to the bloodstream the acidified physiological saline formulation may prove preferable, or either preparation may be neutralized by dilution in a neutralizing physiological excipient, such as a phosphate buffered saline, just prior to administration.

D. In vitro Properties of N-type VSCC Blocking compounds

This section describes some of the in vitro properties of N-type VSCC blocking compounds, as exemplified by a specific group of omega conopeptides, namely those omega conopeptides that, like omega conopeptide MVIIA, exhibit high affinity binding to the MVIIA (site 1) binding site and relatively low affinity binding to the SVIB (site 2) omega conopeptide binding site, as discussed below.

1. Calcium-Channel Antagonist Activity. Omega conotoxins bind to a specific population of binding sites, present mainly in neuronal tissue. Dihydropyridines and other L-type channel blockers do not displace omega conotoxin binding, nor do omega conotoxins displace binding of such L-channel specific ligands to L-type calcium channels. These observations indicate that L-type calcium channel blockers and N-type calcium channel blockers act at distinct channels. Unlike L-type calcium channels, N-type or omega channels are found predominantly, although not exclusively, in nervous tissue (Sher, et al., 1991).

Inhibition (blockade) of N-type or omega HVA neuronal calcium channels can be conveniently measured in an isolated cell system, such as the mouse neuroblastoma cell line, strain N1E115 or the human neuroblastoma cell line IMR32, as described in U.S Pat. No. 5,364,842. As demonstrated therein, N-type calcium currents are blocked by omega conopeptide MVIIA, but not by dihydropyridines.

2. Specific, High Affinity Binding to OCT Receptors. Omega-conopeptides have been shown, in accordance with the invention, to bind with high affinity to specific binding site(s) in neuronal cells. In accordance with the selectivity of the compound, the binding affinity can be characterized either by the binding constant of the compound for the high-affinity MVIIA (SNX-111) binding site, also referred to as "site 1" herein, or the binding constant of the compound for the high-affinity SVIB (SNX-183) or the MVIIC (SNX-230) binding site, also referred to as "site 2" herein. Characteristics of these two distinct OCT binding sites are summarized below. In some cases, it is useful to characterize omega-conopeptides according to the ratio of their binding constants measured for binding to neuronal-cell MVIIA (SNX-111)-specific binding site 1 and SVIB (SNX-183)- or MVIIC (SNX-230)-specific binding site 2.

Binding to the OCT MVIIA binding site in neuronal tissue can be demonstrated in a variety of cell types and synaptosomal cell fractions. One preferred synaptosomal fraction is a mammalian brain synaptosomal membrane preparation, such as the rat brain synaptosome preparation described in U.S. Pat. No. 5,364,842. The binding constant of a compound for the MVIIA binding site is typically determined by competitive displacement of radiolabeled OCT MVIIA (SNX-111) from the synaptosomal preparation, as follows.

The binding constant ($K_d$) of the MVIIA (SNX-111) peptide for the synaptosomal membranes is determined by a saturation binding method in which increasing quantities of radiolabeled peptide are added to the synaptosomal membranes, and the amount of labeled material bound at each concentration is determined (Example 2A). The appropriate binding equation describing the concentration of bound ligand as a function of the total ligand in equilibrium is fitted to the data to calculate the $B_{max}$ (the concentration of binding sites on the synaptosomes), and the $K_d$ (which is approximately the concentration of the ligand required for half saturation of binding sites).

Using conventional Scatchard analysis, a $K_d$ binding value of approximately 10 pM is obtained for omega conopeptide MVIIA. Similarly $K_d$'S were determined for binding of radiolabelled SVIB (SNX-183) and MVIIC (SNX-230) to binding sites in synaptosomal membranes.

Figure 3B:
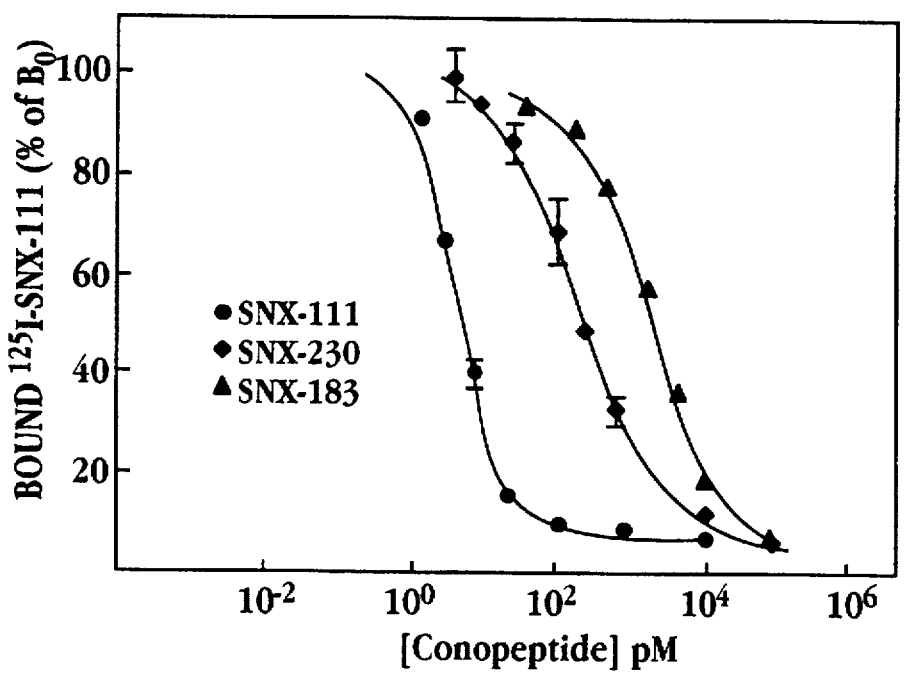

To determine the binding constant of a test N-type VSCC blocking compound for an OCT binding site, the test compound is added, at increasing concentrations, to a membrane preparation, such as a synaptosome preparation, in the presence of a standard concentration of a radiolabeled OCT which exhibits reversible binding, such as OCT MVIIA (SNX-111). The synaptosomal material is then rapidly filtered, washed and assayed for bound radiolabel. The binding constant ($K_i$) of the test compound is determined from computer-fit competitive binding curves, such as shown in FIGS. 3A and 3B for MVIIA (SNX-111) peptide, to determine first the $IC_{50}$ value of the compound, i.e., the concentration which gives 50% displacement of labeled MVIIA peptide. A $K_i$ is determined according to standard methods from the $K_d$ value of OCT MVIIA and the $IC_{50}$ value of the compound, as detailed in Example 2. A relative potency value can also be calculated from this information, as illustrated. Like the $K_i$ value, this value allows comparisons between assays performed under slightly differing conditions or at different times. While the specific value for a particular compound may vary from preparation to preparation, the rank order of binding affinities among the compounds should remain essentially unchanged. Thus the potency of a particular compound can be compared to standard compounds within a given preparation, to determine whether the test compound within a potency range considered useful in the methods of the invention, as discussed below.

Calculated $IC_{50}$ values for a number of omega-conopeptides for binding of OCT MVIIA (SNX-111) to a rat synaptosomal preparation are given in Table 1. The compounds are arranged in order of increasing $IC_{50}$ values.

TABLE 1

COMPETITION OF $^{125}$I-MVIIA (SNX-111) BINDING BY OCT PEPTIDES

| | $IC_{50}$ (nM) |
|---|---|
| SNX-207 | .007 |
| SNX-194 | .008 |
| SNX-195 | .009 |
| MVIIA (SNX-111) | .010 |
| SNX-190 | .021 |
| SNX-236 | .030 |
| SNX-200 | .039 |
| SNX-201 | .046 |
| SNX-202 | .046 |
| SNX-193 | .070 |
| SNX-194 | .090 |
| SNX-239 | .090 |
| MVIIC (SNX-230) | .32 |
| MVIIB (SNX-159) | .101 |
| GVIA (SNX-124) | .134 |
| SNX-198 | .160 |
| SNX-191 | .165 |
| TVIA (SNX-185) | .228 |
| SNX-196 | .426 |
| RVIA (SNX-182) | .893 |
| SVIB (SNX-183) | 1.5 |
| GVIIA (SNX-178) | 3.70 |
| SNX-197 | 11.3 |
| SVIA (SNX-157) | 1460. |

Figure 4A:
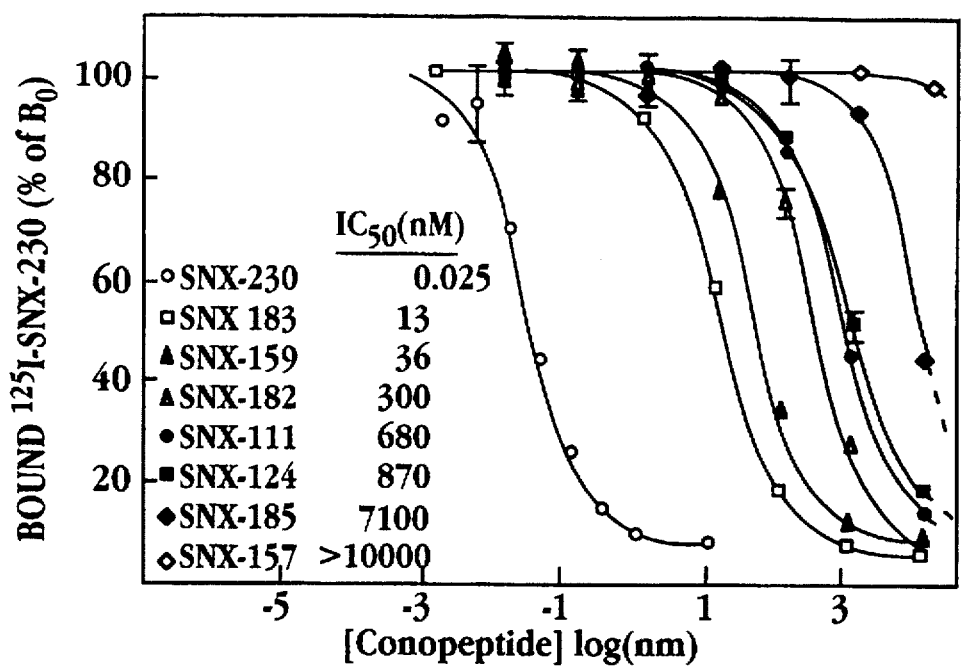
FIGS. 4A and 4B show computer-fit competitive binding curves for omega-conopeptide binding to the OCT MVIIC (SNX-230) binding site in rat brain synaptosomes.
Figure 4B:
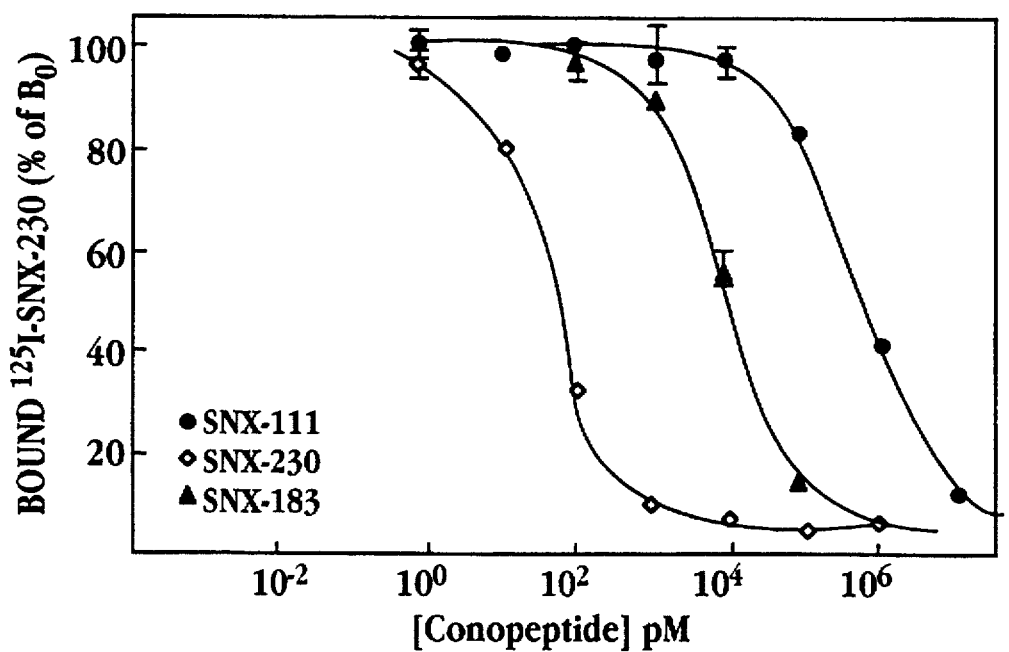

Similarly, $IC_{50}$ and $K_i$ values for compound binding to the SVIB (SNX-183) binding site can be calculated, as above, by determining the $K_d$ of labeled OCT SVIB (SNX-183) or OCT MVIIC (SNX-230) binding to a synaptosome preparation, then using competitive displacement of the labeled compound by the test compound, to determine the $IC_{50}$ and $K_i$ or relative potency values of the test compound. FIGS. 4A and 4B show computer-fit competitive binding curves for several omega-conopeptides whose binding to the SVIB (SNX-183) and/or MVIIC (SNX-230) binding sites was examined. From these curves, $IC_{50}$ values were determined as above.

Tables 2 and 3 list the relative potencies for binding of various omega-conopeptides to the site 1 and site 2 binding sites, and show the ratio of Ki or $IC_{50}$ values determined for binding of each compound to the sites.

TABLE 2

SELECTIVITY OF CONOPEPTIDES FOR SITE 1 AND SITE 2

| | Ki (nM) for competition[a] with: | | Selectivity[b] for: | |
|---|---|---|---|---|
| Compound | [$^{125}$I]-SNX-111 | [$^{125}$I]-SNX-230 | site 1 | site 2 |
| SNX-111 | 0.002 | 150 | 75,000 | 1 |
| SNX-183 | 0.43 | 6 | 14 | 1 |
| SNX-230 | 0.20 | 0.03 | 1 | 7 |

[a]Ki values were derived from analysis of competitive binding performed as described in FIG. 1.
[b]Selectivity is expressed as the ratio of the Ki value determined for competition with high-affinity [$^{125}$I]-SNX-230 binding divided by the Ki value for competition with [$^{125}$I]-SNX-111 binding.

TABLE 3

SELECTIVITY OF CONOPEPTIDES FOR SITE 1 AND SITE 2

| | $IC_{50}$ (nM) for competition with: | | Selectivity[a] for: | |
|---|---|---|---|---|
| Compound | [$^{125}$I]-SNX-111 | [$^{125}$I]-SNX-230 | site 1 | site 2 |
| SNX-199 | 0.09 | 5,000 | 56,000 | 1 |
| SNX-236 | 0.03 | 1,500 | 50,000 | 1 |
| SNX-239 | 0.09 | 10,000 | 111,000 | 1 |

[a]Selectivitty is expressed as the ratio of the $IC_{50}$ value determined for competition with [$^{125}$I]-SNX-230 binding divided by the $IC_{50}$ value for competition with [$^{125}$I]-SNX-111 binding.

3. Selective Inhibition of Neurotransmitter Release. Omega-conopeptides inhibit neurotransmitter release in various regions of the nervous system. As shown below, such inhibition varies according to the neurotransmitter, the omega-conopeptide, and the region studied. Neurotransmitters which can be measured, in accordance with various aspects of the invention, include, but are not limited to dopamine, norepinephrine, acetylcholine, GABA, glutamate, and a number of peptide neurotransmitters, such as calcitonin gene-related peptide (McGeer, et al., 1987).

Quantitation of release and inhibition thereof is determined by sensitive detection methods, also known in the art, including direct detection of release of endogenous stores by HPLC or specific radioimmunoassay (RIA), and detection of release of pre-loaded, labeled compound. Alternatively, or in addition, detection of release may be achieved using a number of indirect assays, exemplified by the electrophysiological studies described above, in which whole tissue response to electrical or chemical stimulation is measured.

Inhibition of release of the neurotransmitter norepinephrine from neuronal cells can be assayed in a number of systems known in the art, and, particularly, in mammalian brain hippocampal slices by standard methods, such as detailed in U.S. Pat. No. 5,364,842. According to the data shown therein, SNX-111 inhibits release of norepinephrine with high potency ($IC_{50} \approx 1$ nM) but only partially (approx. 60%). SNX-183 is much less potent ($IC_{50} \approx 180$ nM) but the inhibition is substantially 100%. SNX-230 also inhibits release completely, but in a biphasic manner, inhibiting approximately 50% with high potency ($IC_{50}$=0.02 nM) and 50% with much lower potency ($IC_{50}$=65 nM). These results suggest that such norepinephrine release is mediated by at least two distinct subtypes of presynaptic calcium channels, one of which corresponds to the site 1 receptor identified by high affinity for SNX-111 and the other to the site 2 receptor recognized preferentially by SNX-230.

Further means of measuring inhibition of neuronal transmitter release are isolated tissue assays, such as atrial strip, aorta, vas deferens and guinea pig ileum assays, in which the response to a stimulus, usually an electrical stimulus, is correlated to the amount of neurotransmitter released from neurons innervating the tissue (Kenakin, 1987). In the guinea pig ileum, inhibition of electrically stimulated contractions is correlated with inhibition of acetylcholine release, as demonstrated by the ability of cholinergic agonists to overcome such inhibition. Example 3 describes the preparation and assay in detail. Table 4 shows the $IC_{50}$ values for various omega-conopeptides on contraction of guinea pig ileum in response to electrical stimulation.

TABLE 4

EFFECTS OF CONOPEPTIDES ON ELECTRICALLY
STIMULATED CONTRACTION OF GUINEA PIG ILEUM

| Compound | $ID_{50}$ (nM) |
| --- | --- |
| SNX-111 | 13 |
| SNX-185 | 29 |
| SNX-183 | 91 |
| SNX-157 | >100 |

II. Treatment of Neuropathic Pain

U.S. Pat. No. 5,364,842 describes analgesic properties of selected omega-conopeptides. This discovery was extended to include treatment of neuropathic pain as disclosed in co-owned U.S. patent application Ser. No. 08/049,794, filed Apr. 15, 1993, and incorporated herein by reference. It is the discovery of the present invention that progression of neuropathic pain can be retarded in a subject exhibiting early stage symptoms of neuropathic pain, particularly by providing localized delivery of N-type VSCC blocking compounds to the neuropathic site.

A. Prevention of Progression of Neuropathic Pain

In general, while brain pathways governing the perception of pain are still incompletely understood, sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in nociceptive processing and in the relay of sensations of pain to various regions of the brain. Analgesia, or the reduction of pain perception, can be effected directly by decreasing transmission along such nociceptive pathways. Modulation of nociception is achieved by neural pathways descending from the cortex and hypothalamus to the mesencephalic central grey region, medullary reticular formation, and ultimately, the dorsal horn of the spinal cord. Analgesic opiates are thought to act by mimicking the effects of endorphin or enkephalin peptide-containing neurons, which synapse presynaptically at the C- or A-fiber terminal and which, when they fire, inhibit release of neurotransmitters, including substance P, excitatory amino acids and calcitonin gene-related peptide (CGRP). Descending pathways from the brain are also inhibitory on C- and A-fiber firing.

While neuropathic pain is known to have a number of underlying etiologies, it is characterized by a distinct set of symptoms. As described in greater detail below, these can include enhanced sensitivity to innocuous thermal-mechanical stimuli, abnormal sensitivity to noxious stimuli, tenderness, and spontaneous burning pain. Neuropathic pain is also progressive in nature, in that it generally worsens over time. Known treatment methods treat the symptoms without necessarily lessening the underlying pathology.

Although the present invention should not be limited by a particular theory of underlying mechanism, it has been observed that chronic neuropathic pain in humans is accompanied by changes in excitability of primary nociceptive afferents. This phenomenon is known as "nociceptor sensitization" and is characterized by increased excitability of the afferents to normally subthreshold stimuli. It is the discovery of the present invention that treatment with omega conopeptides and, more generally, N-type VSCC blockers, inhibit this phenomenon.

In accordance with the present invention, omega-conopeptides useful in treating neuropathic pain are also effective in preventing its progression. Such "neuropatholytic" omega-conopeptides may be distinguished and selected by their abilities (a) to inhibit voltage-gated calcium channels selectively in neuronal tissue, as evidenced by the peptide's ability to inhibit electrically stimulated contraction of the guinea pig ileum, and (b) to bind to omega conopeptide MVIIA binding sites present in neuronal tissue. Such binding to omega conopeptide MVIIA binding sites (site 1, as described herein) is selective, as evidenced by relatively high binding affinity at such sites, as compared to binding at an omega conopeptide site 2 (described herein as a high affinity binding site for SNX-230 or SNX-183). Such selectivity can be measured by the selectivity ratio illustrated in Tables 2 and 3, above.

Moreover, in accordance with the invention, it has been found that neuropatholytic omega-conopeptides are effective as analgesic agents both in traditional opiate-sensitive models of nociceptive pain, such as the Rat Tail-Flick test or the rat hind-paw formalin test, as well as in opiate-resistant models of pain, such as chronic constriction injury models of neuropathic pain.

B. Treatment Modes for Preventing Progression of Neuropathic Pain

While the present invention is not intended to be limited by adherence to any particular theory of underlying mechanism, one theory which is consistent with the invention is that acute nociception leads to alteration of signal transduction mechanisms in pain pathways. Under this theory, interference with such signal transduction by blockade of N-type VSCC's prevents this alteration.

It is a discovery of the present invention that N-type calcium channel blocking omega-conopeptides are effective to prevent development of or progression of neuropathic pain, when administered perineurally to affected skin regions characterized by proliferation of neurite outgrowth subsequent to nerve damage.

Perineural administration can be by topical means, either directly or with the use of a transdermal applicator. Alternatively, perineural administration may be effected by subdermal injection. The resulting blockade of calcium channels reduces the heightened sensation produced by transmission through the neurite proliferation. Perineural delivery may also be effected by forming a cuff around the damaged nerve, preferably of a biodegradable matrix which includes a therapeutic N-type calcium channel blocking compound. Alternatively or in addition, the therapeutic compound can be placed in close proximity to the damaged nerve by conjugating the compound to or coating the compound on a nerve splint designed for repairing damaged nerves. Examples of such nerve splints are provided by U.S. Pat. Nos. 4,534,349 and 4,920,962.

Perineural delivery may also be effected by incorporating N-type calcium channel blocking compounds into suture materials, and using these materials to suture damaged tissues. This method is particularly useful for delivery of compound in areas where it is desirable to provide for inhibition of progression of neuropathy concomitant to tissue damage. U.S. Pat. No. 5,308,889 describes a collagen-based suture material that may be suitable for use for therapeutic delivery of N-type calcium channel blocking compounds.

One particularly useful means for delivering compound to perineural sites is transdermal delivery. This form of delivery can be effected according to methods known in the art. Generally, transdermal delivery involves the use of a transdermal "patch" which allows for slow delivery of compound to a selected skin region. Although such patches are generally used to provide systemic delivery of compound, in the context of the present invention, such site-directed delivery can be expected to provide increased concentration of compound in selected regions of neurite proliferation. Examples of transdermal patch delivery systems are provided by U.S. Pat. No. 4,655,766 (fluid-imbibing osmotically driven system), and U.S. Pat. No. 5,004,610 (rate controlled transdermal delivery system).

For transdermal delivery of peptides, such as omega-conopeptides described herein, transdermal delivery may preferably be carried out using iontophoretic methods, such as described in U.S. Pat. No. 5,032,109 (electrolytic transdermal delivery system), and in U.S. Pat. No. 5,314,502 (electrically powered iontophoretic delivery device).

For transdermal delivery, it may be desirable to include permeation enhancing substances, such as fat soluble substances (e.g., aliphatic carboxylic acids, aliphatic alcohols), or water soluble substances (e.g., alkane polyols such as ethylene glycol, 1,3-propanediol, glycerol, propylene glycol, and the like). In addition, as described in U.S. Pat. No. 5,362,497, a "super water-absorbent resin" may be added to transdermal formulations to further enhance transdermal delivery. Examples of such resins include, but are not limited to, polyacrylates, saponified vinyl acetate-acrylic acid ester copolymers, cross-linked polyvinyl alcohol-maleic anhydride copolymers, saponified polyacrylonitrile graft polymers, starch acrylic acid graft polymers, and the like. Such formulations may be provided as occluded dressings to the region of interest, or may be provided in one or more of the transdermal patch configurations described above.

For delayed release, the N-type calcium channel blocking compound may be included in a pharmaceutical composition for formulated for slow release, such as in microcapsules formed from biocompatible polymers or in liposomal carrier systems according to methods known in the art.

For continuous release of peptides, the peptide may be covalently conjugated to a water soluble polymer, such as a polylactide or biodegradable hydrogel derived from an amphipathic block copolymer, as described in U.S. Pat. No. 5,320,840. Collagen-based matrix implants, such as described in U.S. Pat. No. 5,024,841, are also useful for sustained delivery of peptide therapeutics. Also useful, particularly for subdermal slow-release delivery to perineural regions, is a composition that includes a biodegradable polymer that is self-curing and that forms an implant in situ, after delivery in liquid form. Such a composition is described, for example in U.S. Pat. No. 5,278,202.

The method of the invention also includes local administration of compound to those regions of the spinal cord, such as to dorsal horn regions at affected vertebral levels, where polysynaptic relay of pain sensation occurs. This type of local application can be effected by intrathecal administration, as described in above-referenced co-pending application U.S. Ser. No. 08/049,794. Intrathecal administration delivers compound directly to the sub-arachnoid space containing cerebral spinal fluid (CSF). While effective, this method requires precise technical expertise to ensure delivery to the correct spot.

It is appreciated that delivery to spinal cord regions can also be by epidural injection to a region of the spinal cord exterior to the arachnoid membrane. It is further appreciated that when the N-type voltage-sensitive calcium channel (VSCC) blocking compound is an omega conopeptide, it may be advantageous to add to the conopeptide composition means for enhancing permeation of the conopeptide through meningeal membranes. Such means are known in the art and include liposomal encapsulation, or addition of a surfactant or an ion-pairing agent to the peptide composition.

Alternatively, or in addition, increased arachnoid membrane permeation can be effected by administering a hypertonic dosing solution effective to increase permeability of meningeal barriers.

N-type calcium channel blocking compounds can also be administered by slow infusion. This method is particularly useful, when administration is via the intrathecal or epidural routes mentioned above. Known in the art are a number of implantable or body-mountable pumps useful in delivering compound at a regulated rate. One such pump described in U.S. Pat. No. 4,619,652 is a body-mountable pump that can be used to deliver compound at a tonic flow rate or at periodic pulses. An injection site directly beneath the pump is provided to deliver compound to the area of need, for example, to the perineural region.

In other treatment methods, N-type calcium channel blocking compounds may be given orally or by nasal insufflation, according to methods known in the art. For administration of peptides, it may be desirable to incorporate such peptides into microcapsules suitable for oral or nasal delivery, according to methods known in the art.

Efficacy of the foregoing methods of treatment are conveniently measured in the allodynia model described in Example 4 herein. In this model of peripheral neuropathy, it has been observed that neuropathic pain progressively increases over days 1–7 after the nerve insult, with a plateau of pain response thereafter. To measure ability of a compound to prevent such progression, compound is given just before, during or after nerve insult, and threshold pain responses are measured on days 1–7 thereafter. Prevention of progression of neuropathic pain is observed when there is a heightened threshold to pain stimulus during days 1–7 or where there is a prolongation of time to plateau, as compared to control animals. Efficacious dosages and formulations determined in this model are extrapolated to equivalent large animal and human dosages, according to methods known in the art.

C. Therapeutic Indications

As stated above, neuropathic pain may result from a number of separate etiologies. Generally, progression of such pain may be treated according to any of the methods described herein. However, in many cases it will be preferable to treat the pain in a manner that addresses its specific source. For example, when the pain is traceable to injury of a particular nerve fiber, it may be appropriate to treat such pain either by perineural application of compound to the affected nerve or by dermal application of compound to the affected region.

While a discussion of specific formulations and modes of delivery can be found in foregoing Section II.B. and in Section II.F. below, this section sets forth some exemplary indications for which treatment according to the methods of the present invention may have particular therapeutic utility. The indications described below are by no means exhaustive, but are presented to illustrate some of the various therapeutic situations in which neuropatholytic N-type calcium channel blocking compounds can be used.

1. Ophthalmic indications. The eye is a heavily innervated organ. The cornea in particular is heavily innervated with C-fibers, containing an estimated 3–4000 fiber endings per $mm^2$ compared to an estimated 3–600 fiber endings per $mm^2$ of skin. Injury of the nerve fibers can lead to neuropathic pain of ophthalmic origin. In accordance with the present invention, the eye may be treated with N-channel blocking compounds and particularly with omegaconopeptides, to prevent progression of neuropathy. Application of compound may be achieved by topical administration to the eye, or, in more severe cases, by means of suprachoroidal administration. Such administration may be conveniently achieved by providing a suprachoroidal implant which includes, for example, omega conopeptide SNX-111. U.S. Pat. No. 5,164,188 describes a biodegradable implant that is suitable for chronic and controlled administration of compound to the suprachoroidal space. Chronic, implanted therapeutics are also indicated after ophthalmic surgery, such as after surgery for detached retina or macular holes, where nerve damage may result.

2. Dental indications. Delivery of N-channel blocking compounds to regions of dental repair, such as endodontic repair concomitant to a root canal procedure, may be desirable as a means of preventing progression of dental neuropathy. Here, the therapeutic compound may be included in or added to one or more of the polymer based materials or resins inserted into the root canal after removing the pulp from the region, in accordance with standard techniques known in the art.

3. Burn injury. Burn injuries are characterized by primary hyperalgesia to thermal and mechanical stimuli. In accordance with the principles discussed above, treatment of burned regions with N-type calcium channel blocking compounds may reduce progression of the hyperalgesic response by interfering with signal transduction mechanisms of nociceptor sensory receptors. In this embodiment of the invention, the therapeutic compound can be applied directly to the affected regions, or can be applied in a formulation that includes a protective biopolymer matrix, such as an artificial skin matrix.

4. Reflex sympathetic dystrophy (RSD). RSD is thought to be due to abnormalities in the peripheral nervous system, and more particularly, to sensitization of cutaneous somatosensory afferents. Sympathetic outflow is thought to activate foci of ectopic neural hyperexcitability. Treatment of this condition to prevent its progression may be effected by any of the various dermal (topical) or subdermal routes of delivery discussed above. Perineural delivery may also be indicated for this condition.

5. Post-herpetic neuralgia. Post-herpetic neuralgia is characterized, in its acute phase, by intraneural inflammation which can cause damage to primary afferent axons. This damage may result in abnormal sensitivity to cutaneous stimuli. In general, the mode of treatment to prevent progression of abnormal sensitivity will depend on the location in the body of the affected nerve(s). Perineural or topical delivery of therapeutic N-type calcium channel blocking compound is indicated in this condition.

6. Diabetic neuropathy. Neuropathy of primary afferent axons in long nerves is found in diabetic patients. This results in the dying-back and attempted regeneration of distal tips of primary afferent axons of these nerves. Nociceptor sensitization may ensue. Such sensitization and its progression may be treated according to one or more of the treatment methods described herein. In particular, perineural or topical application of therapeutic compound will be indicated, in accord with the location of the affected nerve and nerve beds.

7. Arthritis. Arthritis is characterized by enhanced sensation of pain via articular afferents. N-type calcium channel blocking compounds find utility in treatment of such pain according to the principles set forth in the present invention. Generally, in treating articular afferents, therapeutic compound will be administered perineurally, in the vicinity of the affected joint.

D. Omega-Conopeptides

In accordance with this invention, neuropatholytic omega-conopeptides conform to certain physical and chemical constraints, as described below. Generally, omega-conopeptides useful in the treatment methods are those which are 25–35 amino acids in length and which have three disulfide bonds at specified positions along their length.

Based on a sequence homology analysis of the peptides whose full sequences are known (FIG. 1), the naturally occurring active omega-conopeptides were grouped into distinct groups I and II, each with internal homologies distinct to that group, as can be appreciated from FIG. 5. Group I includes active omega-conopeptides MVIIA (SNX-111), MVIIB (SNX-159) and SNX-239, which possess binding constants to the MVIIA site within the range of compounds showing activity in treating pain. Group II includes TVIA (SNX-185), SNX-207 and SNX-236, which also possess binding constants in the range of compounds for analgesia. A third group includes inactive peptides SNX-231, and SVIA (SNX-157) and omega-conopeptides whose binding activities for the MVIIA site on neuronal membranes and/or activity in norepinephrine inhibition are outside the range of active compounds.

The three groups of omega-conopeptides are arranged in FIG. 5 with their six Cys residues aligned, which places these residues at positions 1, 8, 15, 16, 20, and 28. To make this alignment, gaps were introduced at the positions shown in the three groups. In the analysis below, these gaps retain the assigned number shown in FIG. 5, even though they represent amino acid deletions in the respective groups of active omega-conopeptides.

Sequence variation in the peptides, based on primary structure alone, was analyzed by adopting the following constraints:

1. The peptides in both active groups (I and II) include the Cys residues at position 1, 8, 15, 16, 20, and 28. Other Cys residues could be substituted at the positions indicated below only if they are selectively protected during oxidation of the peptide to form the three disulfide linkages.

2. The peptides in the active groups include three disulfide linkages connecting the Cys residues at positions 1 and 16, 8 and 20, and 15 and 28. As described above, the disulfide bridges are formed by air oxidation of the full sequence peptide in the presence of DTT. The ability of the peptide to form the three desired disulfide linkages would therefore require that the peptide, prior to disulfide bridging, be able to adopt a conformation which allows the three selected linkages, with or without the Cys protecting-group strategy discussed above. This constraint would thus exclude amino acid variations which prevent or otherwise hinder the formation of the three selected bridges.

Constraints 1 and 2 preserve the basic conformation of the omega-conopeptides imposed by the three disulfide bridges.

3. Within Group I, the amino acid variations which occur at the six non-conserved residues are allowed, including peptides in which the carboxy terminus is amidated or has a free acid form. That is, the first group compound derivatives include the peptide structures having the form: SEQ ID NO: 22-$X_1$-SEQ ID NO: 23-$X_2$-$X_3$-$X_4$-$X_5$-SEQ ID NO: 24-$X_6$-SEQ ID NO: 25-$X_7$-SEQ ID NO: 26-t, where $X_1$=K or S; $X_2$=S or H; $X_3$=R, L, or A; $X_4$=L or T; $X_5$=M or S; $X_6$=N or a deletion; SEQ ID NO 25 is R; $X_7$=S or deletion, and t=a carboxy or amidated carboxyterminal group, and where SEQ ID NO: 22 is C K G K G A; SEQ ID NO: 23 is C; SEQ ID NO: 24 is Y D C C T G S C; and SEQ ID NO: 26 is G K C.

4. Within Group II, the amino acid variations which occur at the eight non-conserved residues are allowed, including peptides in which the carboxy terminus is amidated or has a free acid form. Thus, the second group compound derivatives include the peptide structures having the form: SEQ ID NO: 27-$X_1X_2X_3$-SEQ ID NO: 28-$X_4$-SEQ ID NO: 31-t, where $X_1$=X or R; $X_2$=T or L; $X_3$=S or M, $X_4$=X or P; and t=a carboxy or amidated carboxyterminal group, and where SEQ ID NO: 27 is C L S X G S S C S; SEQ ID NO: 28 is Y N C C R S C N; and SEQ ID NO: 31 is Y S R K C R.

5. Considering both active groups together, amino acid positions which are conserved in all active species are preserved. Thus, for example, the Cys residues, the 5-position glycine, the 13-position tyrosine, the 19-position serine, and the 26-position lysine are all preserved. Preferred OCT analogs or derivatives may be selected by comparing, for purposes of inter-sequence conservation and substitution, those sequences known to be active. For example, in the case of the treatment of pain, omega-conopeptides MVIIA (SNX-111), SNX-239, SNX-199, TVIA (SNX-185) and SNX-236 are known active compounds. Active derivatives are those peptides having, in addition to the conserved cysteine residues described above, a conserved glycine residue at position 5, conserved serine residues at positions 9, 19, and 24, and a conserved lysine residue at position 26. Inter-sequence substitution of variable residues is then preferable in the formation of active analogs. For example, analog position 2 may be occupied by a lysine or a leucine residue, and position 6 may be occupied by an alanine or a serine residue.

6. Considering both active groups together, there are amino acid positions which are likely to be variable within the range of active species. For example, the position 2 amino acid may be lysine or leucine, the position-3 amino acid may be glycine or serine, and the position 4 amino acid, hydroxyproline or arginine. In addition, if the two or more amino acids at a variant position are in a common substitution class, substitution within that class may be favorable. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions.

7. Considering the known inactive species, substitutions to amino acids which are present in inactive species, but not active ones, at any selected residue position, are not favored to preserve activity in the active compounds. Thus, for example, although a 3-position serine is present in both active and inactive compounds, 4-position serine or threonine is present in inactive species only, and either substitution is thus disfavored.

The above amino acid selection rules 6-7 are intended as a guide for allowed amino acid substitutions within active omega-conopeptides. Once an amino acid substitution or modification is made, the peptide is further screened for the requisite calcium channel antagonist activity, and the requisite activities for inhibition of neurotransmitter release and binding to the appropriate OCT binding site of neuronal membranes, as described above.

Several of the amino acid substitutions or modifications to the omega-conopeptide illustrate the principles outlined above.

Omega-conopeptides which are selected on the basis of these criteria, discussed in detail below, are tested for ability to produce analgesia in a standard test of analgesia, such as the Rat Tail-Flick test, wherein analgesia is measured by a prolongation of reaction time to a noxious radiant heat stimulus.

E. In vitro Properties of Neuropatholytic Omega-Conopeptides

1. Calcium Channel Blocking Activity.

Calcium channel blocking activity was measured electrophysiologically in neuronal (N1E-115 or IMR-32) cell lines, as described in Section II. Omega-conopeptides having calcium channel blocking activity are those which block calcium currents in such cell lines with potencies in the range observed for omega-conopeptides MVIIA and GVIA in N1E-115 cells.

2. High Affinity Binding to OCT Binding Sites. Methods for determination of binding affinity to OCT binding sites are detailed in Examples 2–3, below.

Compounds were tested for their ability to displace binding of SNX-111, SNX-183, or SNX-230 from their respective binding sites (site 1 and site 2, as described above). In displacing SNX-111, it was found that compounds having analgesic activity, such as OCT MVIIA (SNX-111), SNX-239, SNX-236, SNX-199 SNX-159 and TVIA (SNX-185), have $IC_{50}$ values between about 15 and 300 pM, and $K_i$ values between about 1 and 100 pM. In contrast inactive compound SNX-183 had an $IC_{50}$ of greater than 1000 pM for binding at the MVIIA site.

From the foregoing, it is seen that active compounds in accordance with the invention are characterized by a high binding affinity for MVIIA binding site 1. The binding affinity for these sites may be characterized as follows. In the first approach, the binding affinity of the compound for binding site 1, as estimated by $IC_{50}$ in displacing MVIIA from the site, is compared directly with those of selected high affinity active compounds, such as SNX-111 and SNX-185. An active compound is one whose binding affinity is at least as high as and preferably within the range of binding affinities measured for such high affinity OCT's. Secondly, the binding affinity of the test compound can be characterized by binding to binding site 2, as estimated by $IC_{50}$ in displacing MVIIC (SNX-230) or SVIB (SNX-183) from the site. Thirdly, the binding affinity of the compound can be characterized by the ratio of binding constants or relative affinities of the compound for site 1 and site 2, as just described. Here an active compound is one whose binding ratio is within the range for the selected active peptides, such as MVIIA (SNX-111) and TVIA (SNX-185); i.e., the binding ratio is substantially within the range of the ratio observed for the omega-conopeptides MVIIA and TVIA.

A number of omega-conopeptide compounds which were tested gave $IC_{50}$ and $K_i$ values lower than or within the ranges of those of omega-conopeptides MVIIA (SNX-111) and TVIA (SNX-185) for binding at the SNX-111 site, as shown in Table 1, and these compounds should thus be considered candidates as analgesic compounds. In addition active compounds have relatively high selectivities of binding, equivalent or greater than those of MVIIA and TVIA, as shown in Tables 2 and 3. However, some of these compounds, may not fulfill additional criteria for analgesic compounds of the invention, as described herein.

3. Inhibition of neurotransmitter release. Another requisite property of analgesic OCT compounds, in accordance with the invention, is their ability to specifically inhibit depolarization-evoked and calcium-dependent neurotransmitter release from neurons. For example, it is shown here that analgesic omega-conopeptides inhibit of electrically stimulated release of acetylcholine at the myenteric plexus of the guinea pig ileum (Example 3). This inhibition is associated anti-nociceptive activity, as seen in Table 4. Omega-conopeptides having analgesic activity have $IC_{50}$'s in the range of those values observed for active omega-conopeptides MVIIA (SNX-111) and TVIA (SNX-185), or less than approximately 50 nM, as observed in this assay.

4. In vivo Measurements of Neuropathic Analgesia.

Relief of neuropathic pain is conveniently measured in one or more of a number of animal models known in the art, in which an animal's response to a given pain stimulus is measured following experimental production of neuropathy. Inhibition of progression of the neuropathic condition can also be measured in this model, when measurements are taken in individual animals over time following the experimental neuropathic insult. While normal progression of the condition will be expected to result in animals that are increasingly sensitive to a given pain stimulus over time, inhibition of this progression will be observed as a leveling or diminishing of response to pain stimulus with time.

One demonstrated model of neuropathic pain resembles the human condition termed causalgia or reflex sympathetic dystrophy (RSD) secondary to injury of a peripheral nerve. This condition is characterized by hyperesthesia (enhanced sensitivity to a natural stimulus), hyperalgesia (abnormal sensitivity to pain), allodynia (widespread tenderness, characterized by hypersensitivity to tactile stimuli), and spontaneous burning pain. In humans, neuropathic pain tends to be chronic and may be debilitating. This type of pain is generally considered to be non-responsive or only partially responsive to conventional opioid analgesic regiments (Jadad, et al., 1992). In accordance with the invention, neuropatholytic N-type VSCC blocking compounds are effective in providing relief of neuropathic pain, as described below.

Experiments carried out in support of the present invention were performed in a rat model of peripheral neuropathy detailed in Example 4. Briefly, in the model used, rats are subjected to a surgical procedure, described by Kim and Chung (1992) and Bennett and Xie (1988) designed to reproducibly injure peripheral nerves (spinal nerves L5 and L6). These rats develop a hyperesthetic state, which can be measured, using one or more paradigms known in the art. Here, mechanical allodynia was measured by stimulation of neuropathic rat hindlimb using wire hairs having graded degrees of stiffness. Analgesic compounds reverse the heightened sensitivity such animals exhibit to the stimulus.

FIG. 6 shows results in the allodynia test of animals treated with SNX-111 (6A), SNX-239 (6B), SNX-159 (6C) and SNX-230. Data are expressed as percent maximum effect, where the maximum effect indicates a complete reversal of surgically induced allodynia, or relative insensitivity to stimulus (maximum equals 15 gram hair stimulus). A baseline of zero indicates a mean sensitivity to a wire hair graded at less than 3 grams. As shown in FIG. 6A, treatment of rats (n=6/treatment) with 1 or 3 µg SNX-111 resulted in elevation of threshold response. Peak elevation of response due to drug treatment (reversal of allodynia) was observed by 30–60 minutes, and effects lasted in excess of 60 minutes. SNX-239 showed significant analgesic effects at a dose as low as 0.33 µg, and evoked a prolonged analgesic response of at least 2 hours, as indicated. SNX-159 was also effective against neuropathic pain in this test at submicromolar doses (FIG. 6C), while SNX-230was ineffective at such doses (FIG. 6D).

Figure 6A:
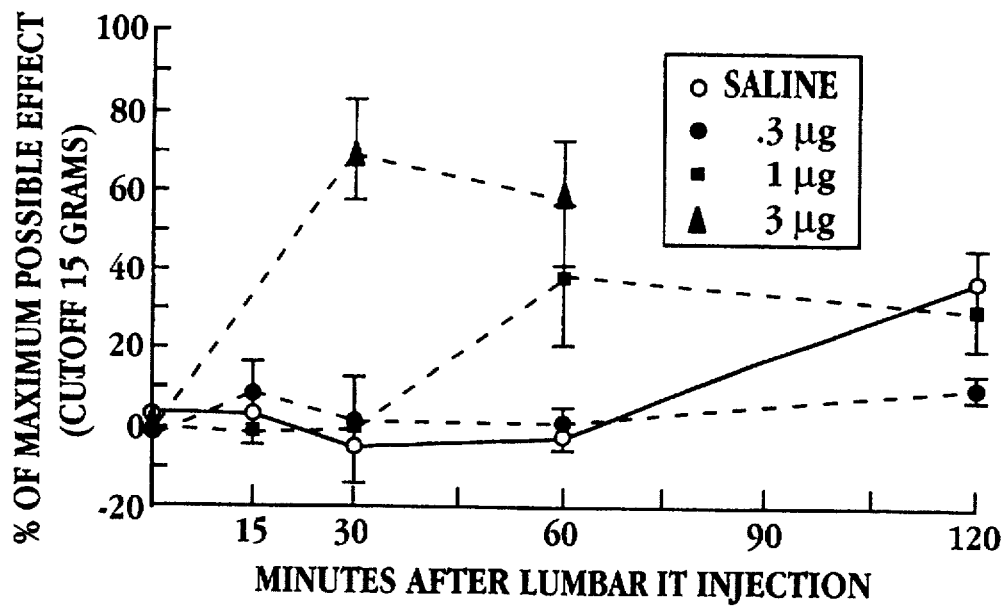
FIGS. 6A–6D show the effect of treatment with various omega-conopeptides on mechanical allodynia thresholds in rats with a painful peripheral neuropathy, where SNX-111 (6A), SNX-239 (6B), SNX-159 (6C) and SNX-230 (6D) were tested at the doses indicated.
Figure 6B:
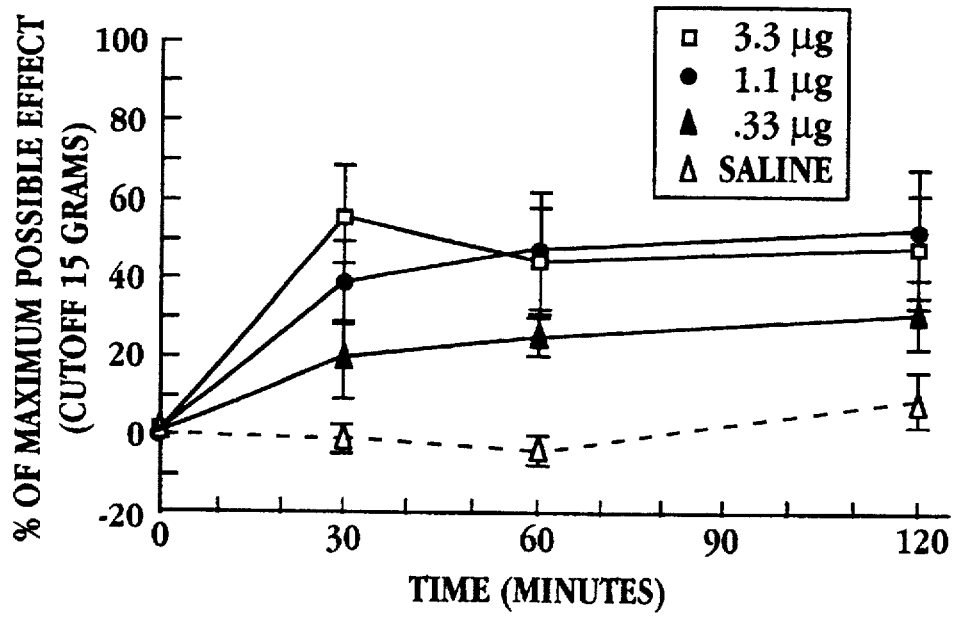
Figure 6C:
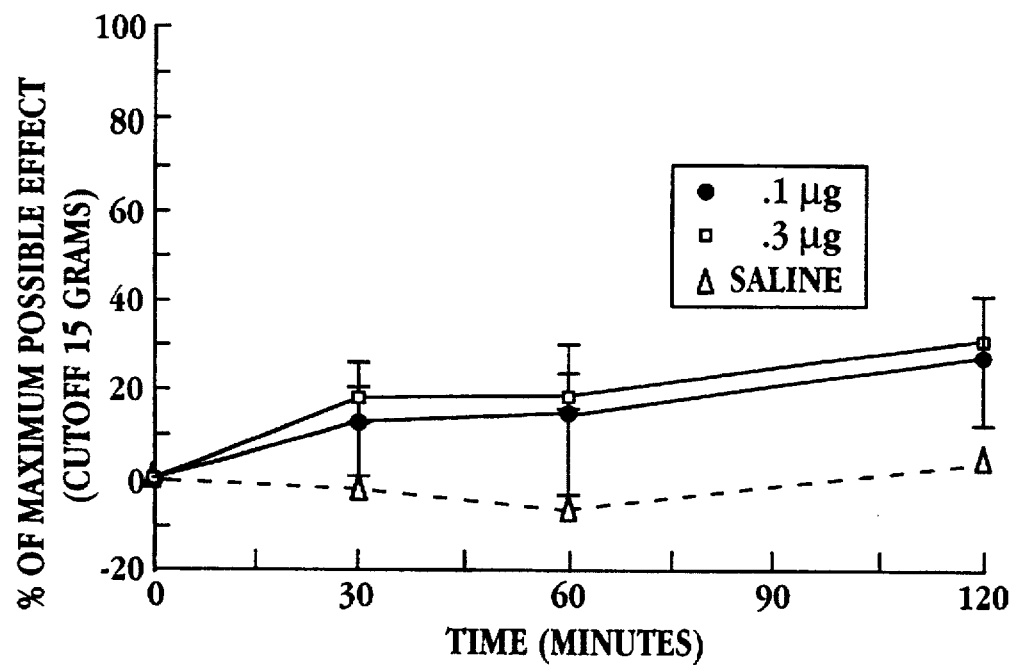
Figure 6D:
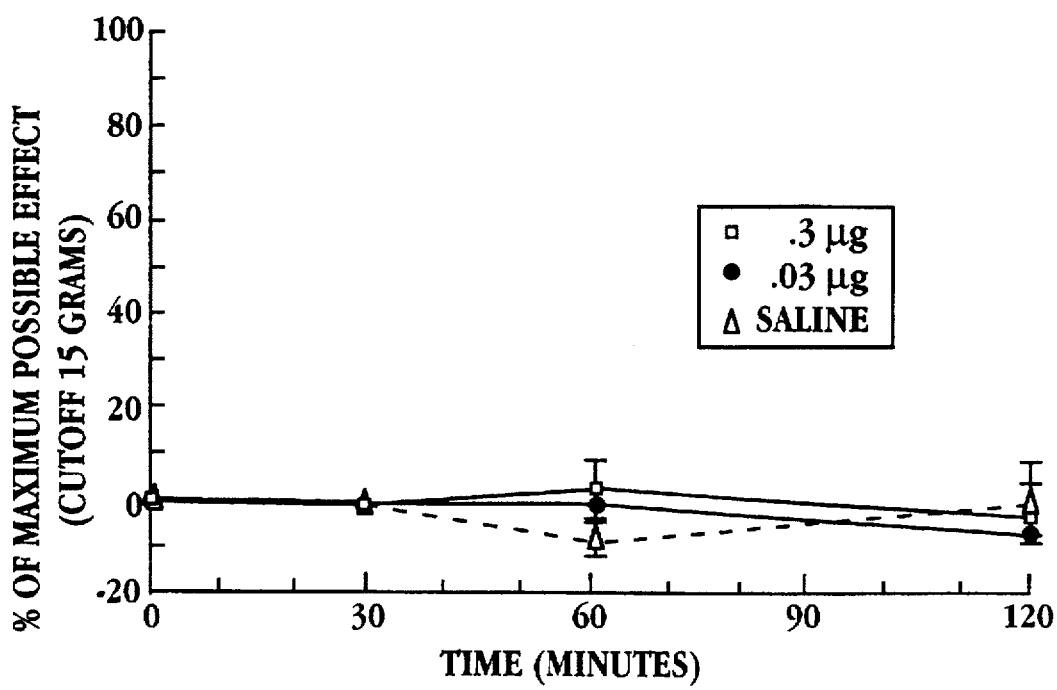
Figure 7A:
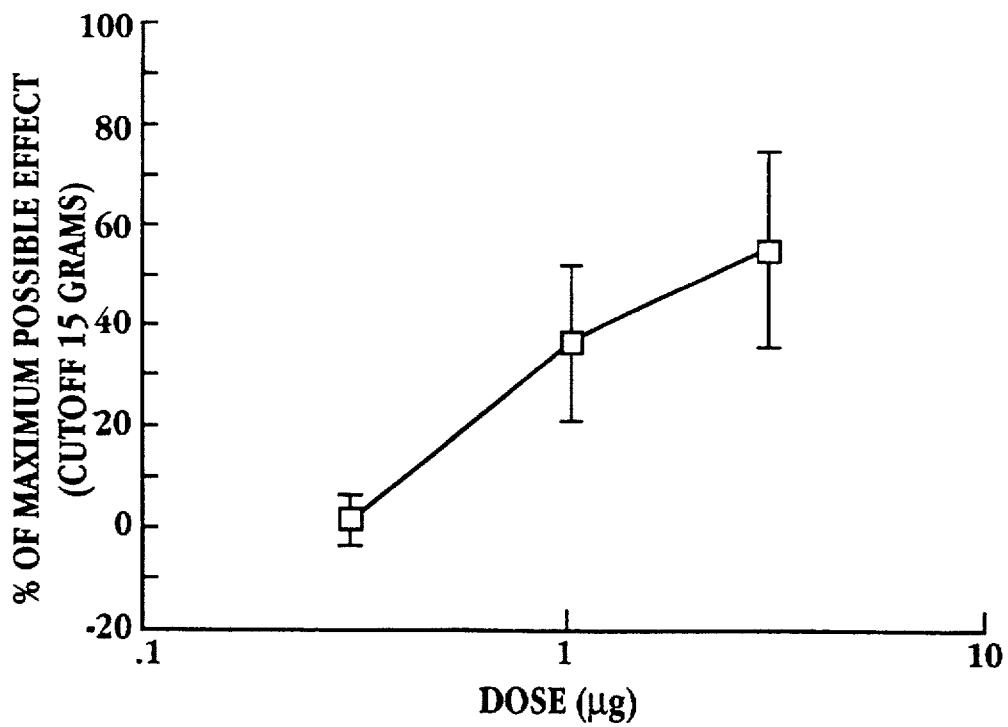
FIGS. 7 (A,B) shows dose response curves of effects of omega-conopeptides SNX-111 (7A) and SNX-239 (7B) derived from the data illustrated in FIGS. 6A and 6B, respectively, in a rat model of neuropathic pain.
Figure 7B:
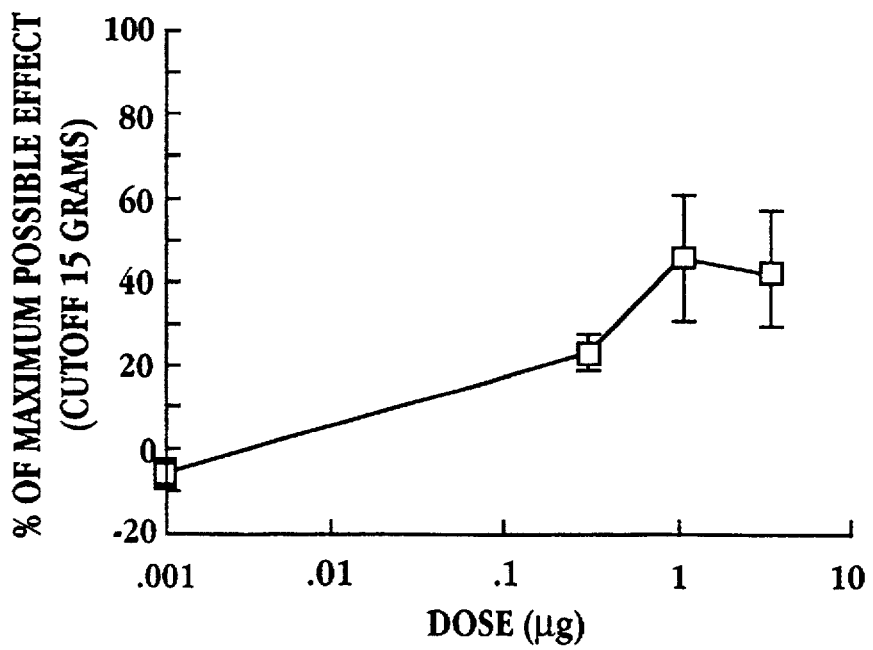

FIGS. 7A and 7B show dose response curves derived from the data shown in FIGS. 6A and 6B. These results indicate that analgesic omega conotoxin peptides, exemplified by SNX-111, are capable of reversing the hyperesthetic effects induced by nerve damage.

F. Dosages and Formulations

From the foregoing, it can be appreciated that treatment with N-channel blocking compounds and, more particularly, omega conopeptides having binding and inhibitory activities within the range of activities defined by omega conopeptides MVIIA (SNX-111) and TVIA (SNX-185) are useful in preventing progression of neuropathic pain. Generally, dosages and routes of administration of the compounds will be determined according to the site of the pain and the size of the subject, according to standard pharmaceutical practices. Intrathecal administration, either as a bolus dosage and as a constant infusion, can be used for treatment and prevention of progression of neuropathic pain. In preferred embodiments, dosages equivalent to at least 0.1–3 µg intrathecal SNX-111 in rats are effective against peripheral neuropathy of the hindlimb. It is also appreciated that compound can be administered perineurally, for example by topical or subdermal application to cutaneous regions having affected nerve endings, according to methods known in the art. In addition, administration may by epidural means, as discussed below.

Figure 9:
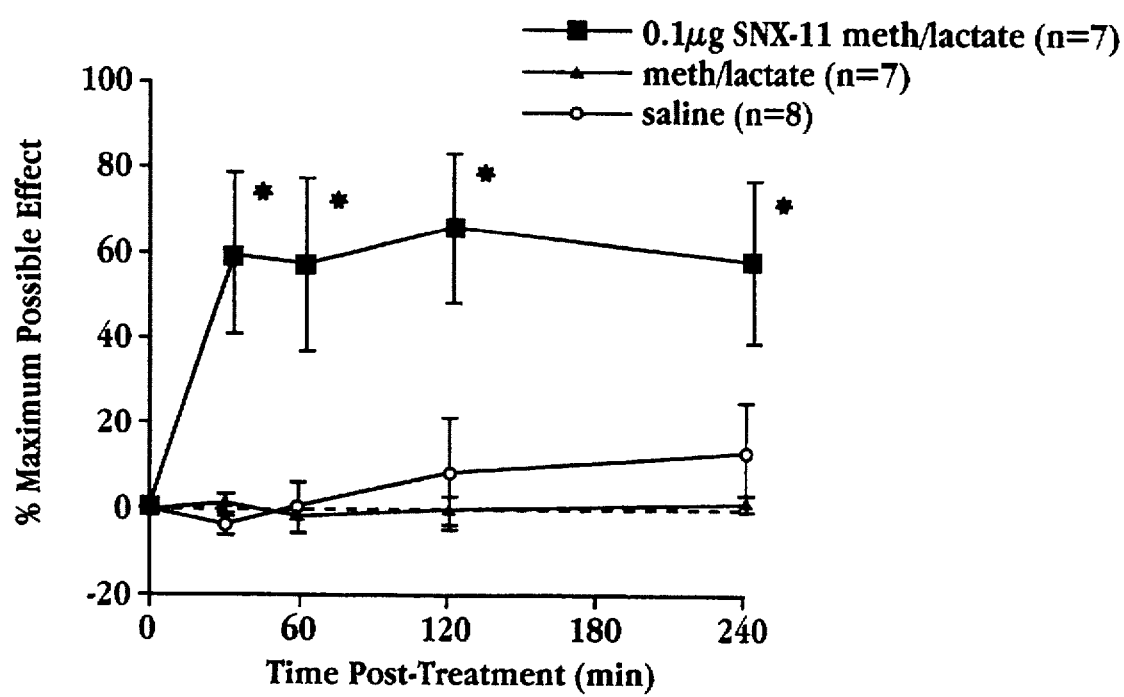
FIG. 9 shows analgesic efficacy of an SNX-111 formulation combining methionine in lactate buffer.

Stabilized formulations, as described in Section I.B above, are useful in storing and administering therapeutic omega conopeptides according to the methods described herein. While it may be desirable to neutralize the solutions prior to administration, formulations utilizing lactate or acidified saline as excipient may also be administered directly via acute intrathecal bolus injection or by other routes for which acidified excipients are appropriately used. Neutralization, if required, can be accomplished by dilution into a pharmaceutically acceptable neutralizing excipient buffer, just prior to injection into the subject. FIG. 9 shows the results of experiments demonstrating that SNX-111 administered as a methionine-lactate formulation was as effective as SNX-111 alone in reducing neuropathic pain.

For some applications, it may be desirable to include in the omega conopeptide composition or treatment regimen means for enhancing permeation of the conopeptide through meningeal tissues which may surround the damaged or target nerve. Means for enhancing transport of compound are known in the art and may include encapsulating the conopeptide in liposomal membranes, addition of a surfactant to the composition, addition of an ion-pairing agent, and the like. Alternatively, or in addition, transmeningeal transport may be facilitated by administering to the subject a hypertonic dosing solution effective to disrupt meningeal barriers, according to methods well known in the art. Alternatively, trans meningeal or transcutaneous transport may be facilitated by modifying the primary sequence of omega-conopeptide, for example by substituting neutral amino acid sidechains or hydrophobic moieties for cationic residues.

The following examples are intended to illustrate various characteristics of the method of the invention, but are in no way intended to limit the scope of the invention.

EXAMPLE 1

Preparation of OCT Peptides

Abbreviations used in this example are BOC, tertiary butoxycarbonyl; DCM, dichloromethane; TFA, trifluoroacetic acid; IPM, N-isopropylmorpholine; BOC-AA-OH, BOC amino acid; DIEA, diisopropylethylamine; 2-ClZ, chlorobenzyloxycarbonyl; tosyl, p-toluenesulfonyl; DMF, N,N-dimethylformamide; TFE, trifluoroethanol; SA, symmetrical anhydride of BOC-AA-OH; DCCI, N,N-dicyclohexylcarbodiimide; E, ethyl ether; P, petroleum ether.

Commercially available benzhydrylamine-resin hydrochloride, Lot No. B30101, was obtained from commercial sources (Beckman Instruments Inc., Palo Alto, Calif. Advanced ChemTech). With this resin, cleavage of a peptide formed on the resin, under the conditions described below, produces a peptide which is amidated at its carboxy end.

A. Preparing Protected Amino Acid Anhydrides Each BOC-AA-OH (2.4 mmol) was dissolved in 5 ml $CH_2Cl_2$ and cooled to 0 C. The volume of DCM used for BOC-Leu-OH (dried in vacuo) was 12 ml, and the BOC-Leu-OH solution was not cooled. 2 ml 0.6 M DCCI in DCM was added and the mixture stirred at 0 C. for 15 min. For BOC-Leu-OH, the mixture was also cooled after this addition. Precipitation of N,N-dicyclohexylurea was completed by storage at −20° C. for 1.5 hour, after which the precipitate was filtered and washed with ethyl ether (5 ml). The filtrate was evaporated to remove solvents and the product was crystallized in the solvent system given in the Table below. Residual amounts of DCM can affect the exact conditions for crystallization. Recrystallization was performed by dissolving in DCM, evaporating most of the solvent, and recrystallizing from the appropriate solvent.

TABLE OF AMINO ACID SOLVENTS

| Amino Acid | Solvent |
| --- | --- |
| Ala | DCM:E:P |
| Asp (Benzyl) | E:P |
| Gly | E:P |
| Leu | P |
| Lys (2-ClZ) | E:P |
| Met | E:P |
| Ser (Benzyl) | E:P |
| Thr (Benzyl) | E:P |
| Tyr (2-BrZ) | DCM:P |

B. Preparation of MVIIA

Synthesis of MVIIA peptide was performed on 0.58 g benzhydrilamine resin (0.40 mmol) in a Beckman Model 990 Peptide Synthesizer by a solid-phase method based on the primary structure shown in FIG. 1A.

A double coupling protocol was used for the incorporation of residues Cys-25 through Tyr-13, and a triple coupling protocol, for amino acids Met-12 through Cys-1. Symmetrical anhydrides were used in crystalline form as described in Yamashiro (1987). Crystalline symmetrical anhydrides (1.0 mmole) were each dissolved in 6 ml DCM and stored in the amino acid reservoirs at 4° C. Sidechain protecting groups used were: Cys, 4-MeBenzyl; Lys, 2-ClZ; Ser, Benzyl; Arg, Tosyl; Thr, Benzyl; Asp, Benzyl; Tyr, 2-Br-Benzyl.

Unless specified, volumes were 8 ml, except for step 2 below, which was 10 ml, and all reactions were carried out at room temperature. After incorporation of the Asp-14 residue, the volume of step 2 was increased to 15 ml while all other volumes were raised to 10 ml after incorporation of the Arg-10 residue. The double coupling protocol consisted of steps 1–16 listed in the Table below.

Amino acids Met-12 through Cys-1 were added by a triple coupling protocol which included, in addition to steps 1–16, steps 17–20 in the MVIIA protocol Table.

MVIIA PROTOCOL TABLE

| Step | Reagent |
| --- | --- |
| 1 | DCM wash (3 times) |
| 2 | 67% TFA/M (20 min.) |
| 3 | DCM wash (2 times) |
| 4 | 25% dioxane/DCM wash (2 times) |
| 5 | 5% DIEA/DCM wash |
| 6 | DCM wash |
| 7 | 5% DIEA/DCM wash |
| 8 | DCM wash (5 times) |
| 9 | 1.0 mmol SA in DCM (5 min) |
| 10 | 0.5 mmol IPM in 3 ml TFE plus 1 ml DCM |
| 11 | (5 min) |
| 12 | 0.5 mmol IPM in 5 ml DCM (5 min) |
| 13 | DMF wash (3 times) |
| 14 | 1.0 mmol SA in DMF (5 min) |
| 15 | 0.5 mmol IPM in 5 ml DCM (5 min) |
| 16 | 0.5 mmol IPM in 4 ml DMF (5 min) |
| 17 | DCM wash |
| 18 | DCM wash (2 timnes) |
| 19 | 1.0 mmol SA in DCM (5 min) |
|  | 0.5 mmol IPM in 4 ml DMF (5 min) |
| 20 | DCM Wash |

Crystalline symmetrical anhydrides (1 mmole) were each dissolved in 6 ml DCM or DMF and stored in the amino acid reservoirs at 4° C. Side-chain protecting groups used were: Cys, 4-MeBzl; Lys; ClZ; Ser, Bzl; Arg, tosyl; Thr, Bzl; Asp, Bzl; Tyr, BrZ.

For BOC-Arg(tosyl)-OH, the following mixture was prepared: 1.87 BOC-Arg(tosyl)-OH, 0.57 g 1-hydroxybenzotriazole, 15 ml DMF, stirred to dissolve, cooled to 4° C. added 0.52 ml diisopropylcarbodiimide, and split in half for steps 9 and 13. For this coupling, the protocol was modified as follows: step 8 was 3 times DCM wash and 2 times DMF wash; step 9 was for 10 min; step 11 was for 10 min; step 13 was for 10 min; step 14 was 0.4 mmol IPM in 4 ml DMF for 10 min; step 15 was for 10 min; step 16 was 1 times DMF wash and 1 time DCM wash. Reaction mixtures in steps 9, 10, 13, 14 and 18 were not drained.

The mixture for a third coupling for incorporating the Arg-10 residue consisted of 1.00 g BOC-Arg(tosyl)-OH, 1 ml DMF, 5 ml DCM, stirred to dissolve, and cooled to 4° C. to which is then added 1.67 ml 0.6M DCCI in DCM.

After the last amino acid had been incorporated, the protected peptide resin was subjected to steps 1–4 to remove the N-terminal BOC group, collected on a filter with use of ethanol, and dried in vacuum to yield 2.61 g.

MVIIA has also been successfully synthesized on an ABI 430A synthesizer using slight modifications of the above protocol.

C. Deblocking and Cleavage in Liguid HF

A mixture of protected peptide resin (1.32 g), 2-mercaptopyridine (0.50 g), p-cresol (2.6 g), and liquid hydrogen fluoride (HF) (25 ml) was stirred at 0° C. for 80 min. The liquid HF was evaporated with a rapid stream of nitrogen gas, first below 0° C. then at 24° C. The mixture was stirred in ethyl acetate (25 ml) until a finely divided solid was obtained. The solid was filtered, washed with ethyl acetate, and air dried to yield 1.09 g. This solid was stirred in 50% aqueous acetic acid (10 ml) to dissolve the peptide material, filtered, and washed with 20 ml water. The filtrate was freeze-dried to yield 450 mg of fluffy powder.

D. Formation of Disulfide Bridges

A sample (300 mg) of the fluffy powder was dissolved in 30 ml of 0.05M ammonium bicarbonate, 10 mM dithiothreitol (DTT), and 2M guanidine hydrochloride. The solution, which had a pH of 6.7, was allowed to stand at 24° C. for 2 hr. then diluted with 120 ml of water and stirred for 20 hr at 24° C. DTT (25 mg) was added and the solution allowed to stand at 24° C. for 80 min. The mixture was then stirred at 4° C. for 3 days.

E. Isolation of MVIIA OCT

The solution from Part D was acidified with glacial acetic acid (2 ml), evaporated in vacuo to a low volume, and fractionated by gel filtration on Sephadex G-25 in a 2.5×48 cm column, using 1N acetic acid, to remove peptide polymeric species (exclusion volume), and salts (slowest moving peak). Fractions (5 ml) were collected, with peptide absorbance monitored at 280 nm. Fractions corresponding to the monomer peptide were pooled and freeze-dried to give 127 mg of fluffy powder. A sample of the monomeric material (34 mg) was purified by preparative HPLC on a Vydac 218 TP1022 column with a gradient of 10–20% acetonitrile in 0.1% trifluoroacetic acid over 50 min at 8 ml/min, with detection at 226 nm and collection of 4 ml fractions. Fractions corresponding to the major peak were pooled, evaporated in vacuo to remove acetonitrile, and freeze-dried to yield 7.7 mg. Analytical HPLC on a Vydac 218 TP104 column with the same solvent and gradient over 10 min followed by 10 min of isocratic elution at the 20% composition (1.5 ml/min) gave a single peak identical in behavior to an authentic sample of OCT MVIIA. Amino acid analysis of a 24-hr HCl-hydrolysate gave: Asp, 0.93; Thr,1.05; Ser, 2.85; half-cystine, 5.2; Gly, 4.08; Ala, 1.07; Met 0.94; Leu, 1.02; Tyr,0.85; Lys, 3.98; Arg, 2.09.

F. Radio-Iodination of MVIIA MVIIA peptide was iodinated by reaction with Iodogene™ in the presence of NaI according to Cruz et al., with minor modification. 2 m Ci of carrier-free $Na^{125}I$, 75 ul 0.5M phosphate buffer pH 7.4 and 20 ul of 1 ug/ul peptide were added to a polypropylene test tube coated with 10 ug Iodogenf™. The tube was agitated for 8 minutes, and the solution was chromatographed by HPLC through a 10×0.46 cm C-8 reverse phase column with a pore size of 300 Å (Brownlee Labs, Santa Clara, Calif.). The sample material was eluted with a gradient from 0.1% trifluoroacetic acid to 60% acetonitrile in 0.1% trifluoroacetic acid. The major peak of active radio-iodinated peptide was resolved at about 2 minutes greater retention time than the underivatized peptide.

The fractions containing this peak were collected and later diluted for use in binding experiments. MVIIA, iodinated under the conditions as above except with non-radioactive NaI, was tested for the ability to inhibit depolarization-dependent ATP release from synaptosomes as described in Ahmad and Miljanich (1988) and found to be as potent in this regard as the underivatized peptide.

G. Synthesis of Other OCT Peptides

Synthesis of other OCT peptides was according to the solid-phase method described above, except that a single coupling protocol involving steps 1–12 in Part C was used for coupling the first 10 C-terminal amino acids residues, and a double coupling method involving steps 1–16, Part C was used for coupling the final n⁻10 N-terminal residues, where n is 24–29. Releasing the peptide from the solid support, removing the blocking groups, and joining the disulfide bridges were carried out substantially as above, or as described in Part H, below. The peptide was separated from salts and polymeric peptide species by gel filtration on Sephadex G-25, and purified on preparative HPLC. For binding studies, each peptide can be radioiodinated essentially as above.

H. Alternate Oxidation Methods

Two alternative oxidation methods were used in the preparation of MVIIA/SNX-111.

1. The lyophilized crude linear peptide was dissolved in 3M guanidine hydrochloride and 1.2M ammonium acetate solution to yield a concentration of approximately 12 mg peptide/ml. DTT was added to a ratio of 15 mg DTT per 100 mg peptide, and the mixture was stirred at room temperature for 1 hour. The solution was diluted 6-fold with distilled water, and stirred at 4° C. for 3–5 days. The progress of peptide oxidation was monitored by HPLC. The endpoint of the oxidation process was the complete disappearance of free thiols, determined by Ellman reaction.

2. The lyophilized crude linear peptide was dissolved in 3M guanidine hydrochloride and 0.3M potassium phosphate solution to yield a concentration of approximately 12 mg peptide/ml. After addition of 40 mg cysteine and 15 mg DTT per 100 mg peptide, the pH of the solution was adjusted to 8.0–8.1 with potassium hydroxide solution. The mixture was stirred at room temperature for 1 hour. The peptide solution was diluted 6-fold with water, and stirred at 40° C. for 3–5 days. The progress of peptide oxidation was monitored by HPLC. The endpoint of the oxidation process was the complete disappearance of free thiols, determined by Ellman reaction. (Method 2 was used in the preparation of SNX-236 and SNX-239).

Following oxidation by either of the above methods, the solution was acidified with acetic acid to pH 3, and lyophilized.

EXAMPLE 2

Omega-conopeptide Binding to Omega-conopeptide Binding Sites in Synaptosomal Membranes A. Preparation of Mammalian-Brain Synaptosomes and Synaptosomal Membranes Synaptosomes were prepared from rat whole brain or hippocampal region of brain. Rats were sacrificed, and forebrains were removed and transferred to 10 ml ice-cold 0.32M sucrose containing the following protease inhibitors (PI): 1 mM EGTA; 1 mM EDTA; 1 uM pepstatin; 2 uM leupeptin. Brains were homogenized using a motor-driven Teflon-glass homogenizer (approx. 8 passes at 400 rpm). Homogenates from 4 brains were pooled and centrifuged at 900×g for 10 minutes at 4° C. Supernatants were then centrifuged at 8,500×g for 15 minutes. Resulting pellets were resuspended in 10 ml each ice-cold 0.32M sucrose plus PI with vortex mixing. The suspension was then centrifuged at 8,500×g for 15 minutes. Pellets were resuspended in 20 ml ice-cold 0.32M sucrose plus PI. The suspension (5 ml/tube) was layered over a 4-step sucrose density gradient (7 ml each: 1.2M sucrose, 1.0M sucrose, 0.8M sucrose, 0.6M sucrose; all sucrose solutions containing PI). Gradient tubes were centrifuged in a swinging bucket rotor at 160,000×g for 60 minutes at 4° C. The 1.0M sucrose layer plus the interface between the 1.0 and 1.2M sucrose layers were collected and diluted with ice cold deionized water plus PI to yield a final sucrose concentration of 0.32M. The resulting suspension was centrifuged at 20,000×g for 15 minutes. Pellets were then resuspended in 5 ml icecold phosphate buffered saline plus PI. The resulting rat brain synaptosomes were then aliquoted and stored in a liquid nitrogen containment system.

Prior to use in binding assays, synaptosomes were thawed and diluted with 3 volumes of ice cold deionized water plus PI. This suspension was homogenized using a PT 10-35 Polytron (setting 6) for two 10-second bursts. The homogenate was centrifuged at 40,000×g for 20 minutes at 4° C. The resulting pellets were resuspended in about 5 ml of ice cold phosphate buffered saline plus PI. The resulting brain synaptosomal membrane preparation was aliquoted and stored at −80° C. until use. Protein concentration of the membrane preparation was determined using Bradford reagent (BioRad), with bovine serum albumin as standard.

B. Saturation Binding Assay MVIIA OCT was radiolabeled with $^{125}$I-iodine by reaction with Iodogen™, essentially according to the method of Ahmad and Miljanich (1988). Following the Iodogen reaction, the peptide solution was chromatographed by HPLC through a C-8 reversed phase column and eluted with a gradient from 0.1% trifluoroacetic acid in water to 0.1% trifluoroacetic acid in water/acetonitrile (40:60 vol/vol). The major peak of radioactivity following the underivatized MVIIA OCT was collected.

The binding constant ($K_d$) for [$^{125}$I]-MVIIA OCT to rat brain synaptosomal membranes was determined by a saturation binding method in which increasing quantities of [$^{125}$I] MVIIA OCT were added to aliquots of a synaptosomal membrane preparation (10 ug membrane protein, suspended in binding buffer consisting of 20 mM HEPES, pH 7.0, 75 mM NaCl, 0.1 mM EGTA, 0.1 mM EDTA, 2 µM leupeptin, 0.035 µg/ml aprotinin, and 0.1% bovine serum albumin (BSA), in a total volume of 0.5 ml). Binding at each concentration of labeled compound was determined in the absence and presence of 1 nM unlabeled MVIIA OCT to determine specific binding (as described in part B, below). The amount of labeled peptide specifically bound at each concentration was used to determine $B_{max}$, the concentration of specific binding sites on the synaptosomes, and $K_d$, following standard binding analysis methods (Bennett, et al., 1983). Scatchard analysis of saturation binding curve of [$^{125}$I]MVIIA revealed a $K_d$ of about 10 pM for the compound.

B. Competitive Displacement Binding Assay

1. Competitive Displacement of OCT MVIIA.

Rat brain synaptosomal membranes prepared as described in Part A were suspended in a binding buffer consisting of 20 mM HEPES, pH 7.0, 75 mM NaCl, 0.1 mM EGTA, 0.1 mM EDTA, 2 µM leupeptin, 0.035 µg/ml aprotinin, and 0.1% bovine serum albumin (BSA). [$^{125}$I]-MVIIA (SNX-111) OCT (25–30,000 cpm, approximately 1500–2000 Ci/mmol) and test compound were aliquoted into polypropylene tubes, in the absence or presence of 1 nM MVIIA (SNX-111) OCT to determine non-specific binding. The membrane suspension was diluted and aliquoted last into the test tubes, such that each assay tube contained 10 µg membrane protein and the total volume was 0.5 ml. After incubation for 1 hour at room temperature, tubes were placed in an ice bath, then filtered through GF/C filters (Whatman), which were pre-soaked in 0.6% polyethyleneimine and prewashed with wash buffer (20 mM HEPES, pH 7.0, 125 mM NaCl, 0.1% BSA) using a Millipore filtration system. Just prior to filtration, each assay tube received 3 ml ice-cold wash buffer. The filtered membranes were washed with two 3 ml volumes of ice-cold wash buffer, dried, and filter-bound radioactivity was measured in a Beckman gamma counter (75% counting efficiency).

Representative displacement binding curves for rat brain synaptosomal membranes are illustrated in FIG. 3. $IC_{50}$ values were computed from line fit curves generated by a 4-parameter logistic function. These values represent the concentration of test compound required to inhibit by 50% the total specific binding of [$^{125}$I]-MVIIA (SNX-111) OCT to rat brain synaptosomal membranes, where specific binding is defined as the difference between binding of [$^{125}$I]-MVIIA (SNX-111) OCT in the absence and presence of excess (1 nM) unlabelled MVIIA OCT. Non-specific binding is that binding of radiolabeled compound which is measured in the presence of excess unlabeled MVIIA OCT. Such values serve as approximations of the relative affinities of a series of compounds for a specific binding site.

2. Competitive Displacement of OCT SVIB.

Rat brain synaptosomal membranes were prepared as described above. OCT SVIB was radiolabeled by iodination with $^{125}$I-iodine by the Iodogen reaction. Displacement binding of radiolabeled SVIB on rat brain synaptosomal membranes was carried out as in Example 4B. SVIB displacement curves for several of the omega-conopeptides assayed is shown in FIG. 4. $IC_{50}$ values and relative potency values were calculated as described below. Tables 2 and 3 show the relative potency values for omega-conopeptides examined, and the ratio of relative potencies of the compounds for the OCT MVIIA site and to the SVIB binding site.

The binding constant ($K_i$) for each test substance was calculated using non-linear, least-squares regression analysis (Bennett and Xie, 1988) of competitive binding data from 2 assays performed in duplicate on separate occasions. The relationship between $K_i$ and $IC_{50}$ (concentration at which 50% of labeled compound is displaced by test compound is expressed by the Cheng-Prusoff equation:

$$K_i = IC_{50}/(1+[L]/K_d)$$

where $IC_{50}$ is the concentration of test substance required to reduce specific binding of labeled ligand by 50% ; [L] is the concentration of [$^{125}$I]-MVIIA (SNX-111) OCT used in the experiment; and $K_d$ is the binding constant determined for binding of [$^{125}$I]-MVIIA (SNX-111) OCT to rat brain synaptosomal membranes in saturation binding experiments. Table 3 summarizes computed $IC_{50}$ for various omega-conopeptides for the MVIIA binding site of rat brain synaptosomal membranes.

Relative potency for displacement of binding is calculated as a ratio of the $IC_{50}$ of the test compound and the $IC_{50}$ of the reference compound. The reference compound is generally the unlabeled equivalent of the labeled ligand. Calculation of relative potency is as follows:

$$[\log \text{(relative potency)}] = \log (IC_{50(ref)}) - \log(IC_{50(test)})$$

Relative potency values for binding at OCT MVIIA (SNX-111) and OCT SVIB (SNX-183) sites are listed in Table 3.

EXAMPLE 3

Inhibition of Electrically Stimulated Contractions of Guinea Pig Ileum

Guinea pigs (300–400 gms) were decapitated and the ileum removed. A section of ileum about 6 cm from the caecum was placed immediately into Krebb's modified buffer maintained at 37° C. in a water bath, and aerated with a mixture of 95% $O_2$ and 5% $CO_2$. The buffer contains: KCl, 4.6 mM; $KH_2PO_4$, 1.2 mM; $MgSO_4$, 1.2 mM; Glucose, 10.0 mM; NaCl 118.2 mM; $NaHCO_3$, 24.8 mM; $CaCl_2$, 2.5 mM.

Small pieces of ileum were cut and pulled over a glass pipette, scored and the longitudinal muscle removed. Each piece was attached to an electrode at one end and to a force transducer at the other end. The preparation was lowered into an organ bath maintained at 37° C. and aerated with $O_2$:$CO_2$. The resting tension was set at 1 gm. and the tissue was stimulated at 30–50 V with a duration of 4.5 msec per stimulation.

Baseline responses (contractions) were recorded for 10–15 min. and aliquots (100 ml) of drug were added to the bath until inhibition occurred. Following testing, tissues were washed until original response magnitude was achieved.

EXAMPLE 4

Rat Model of Peripheral Neurovathy

Male Sprague-Dawley rats (250–350 gm) were prepared with chronic lumbar intrathecal catheters inserted under halothane anesthesia (Yaksh and Rudy, 1976). Animals were placed in a prone position and the left paraspinal muscles were separated from the spinous processes at the $L_4$-$S_2$ levels, as described by Kim and Chung (1992). The left L5and L6nerve roots were exposed and tightly ligated with 6–0 surgical silk suture. Approximately 7–10 days after ligation, the lumbar subarachnoid space was catheterized with saline-filled polyethylene (PE-10) tubing as described by Yaksh and Rudy (1976). The Catheter was anchored with stay sutures to the adjacent muscle tissue where it emerged from the cisterna magna. Animals were given at least 3 days to recover before assessing mechanical allodynia thresholds. Allodynia was typically observed to occur beginning 1–2 days post-surgery and continued for as long as 45 days. Animals showing motor deficits were excluded from further study.

For testing, animals were placed in plastic cubicles with open wire mesh bottoms. Compound dissolved in preservative-free saline solution was administered in a volume of 10 µl through the intrathecal catheter, followed by 10 µl saline to flush the catheter line. Animals were tested for allodynia at various time points after drug treatment, as described below.

To assess the threshold of a non-noxious stimulus required to produce a left hind paw withdrawal (allodynia), Von Frey hairs (ranging from 0.4–15 grams), were systematically applied to the surgically treated plantar of the hind paw. The hair was held against the surface with sufficient force to cause slight bending and held for 6–8 seconds. Failure to evoke a response was cause to test the next stiffer hair. Evocation of a brisk withdrawal response was cause to test the next lower stimulus intensity. This paradigm was repeated according to a statistical method (Dixon, 1976) to define the 50% response threshold. Allodynia was evidenced by a threshold less than 3 grams (referring to the hair stimulus intensity) exhibited by all surgically treated animals.

Results of animals treated with saline, or various doses of omega-conopeptides are shown in FIG. 6, FIG. 7 and FIG. 8. Data in FIG. 6 are expressed as percent maximum effect, where the maximum effect indicates a complete reversal of allodynia, or insensitivity to stimulus (maximum equals 15 gram hair cutoff). A baseline of zero indicates a mean sensitivity less than 3 grams. As shown in FIG. 6, treatment of rats (n=6/treatment) with 1 or 3 µg SNX-111 resulted in elevation of threshold response. Peak effects were observed by 30–60 minutes, and effects lasted in excess of 60 minutes.

Figure 8A:
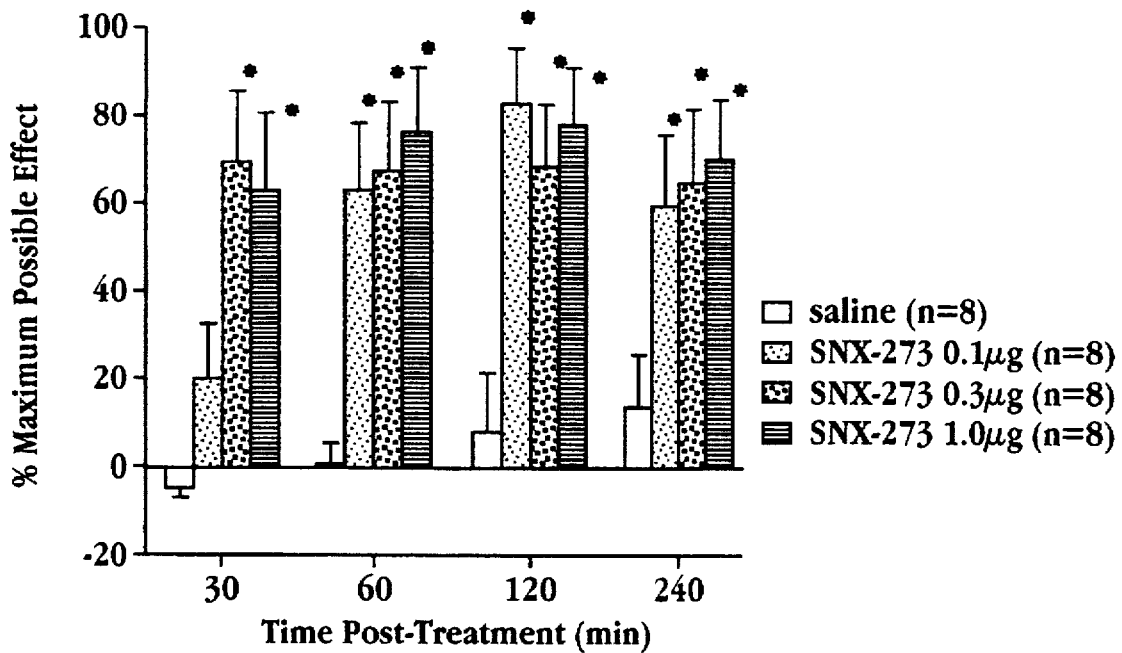
FIGS. 8A and 8B show dose-dependent blockade of mechanical allodynia by SNX-273 (8A) and SNX-279 (8B) in comparison to saline and SNX-111 at various times post treatment, where asterisks indicate statistically significant differences between treatment and saline ($p<0.05$, Student's t test)
Figure 8B:
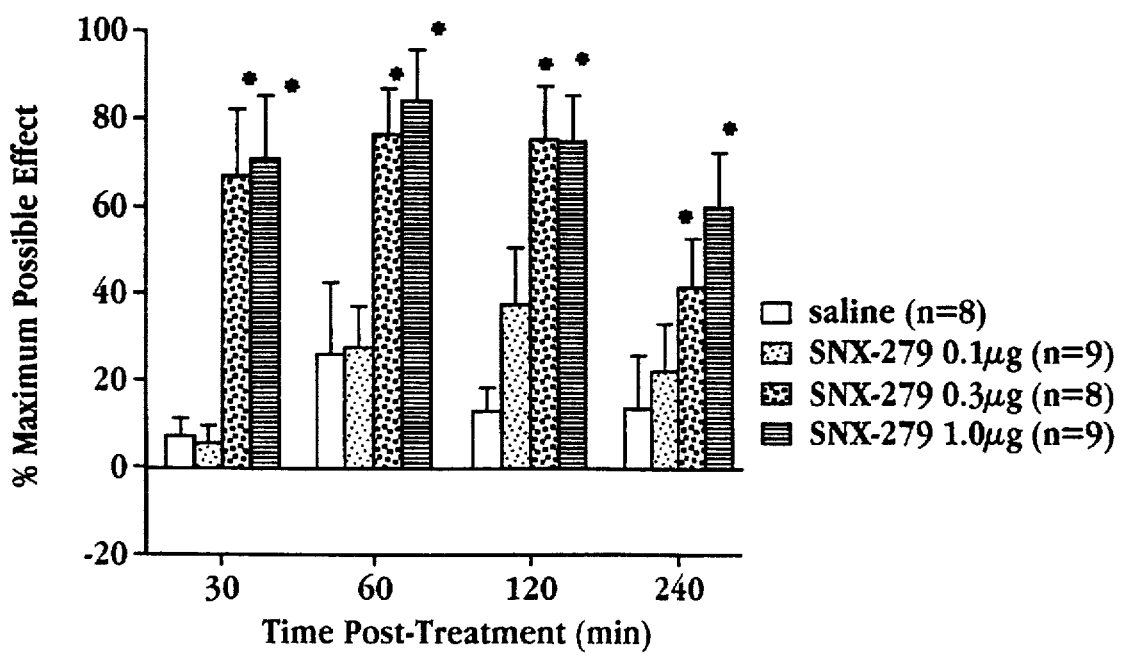

FIGS. 8A and 8B show results of tests in which animals were given a single intrathecal bolus injection of SNX-273 (0.1 µg, 0.3 µg, or 1 µg), SNX-279 (0.1 µg, 0.3 µg, or 1 µg), SNX-111 (0.1 µg) or vehicle (0.9% Sodium Chloride injection, USP, Sanofi Animal Health, Inc., Overland Park, Kans.). Test control compounds were delivered in a volume of 10 µl followed by 10 µl of saline to flush the catheter. Results of allodynia tests, performed as described above, are shown as percentage of maximum possible effect (MPE):

%MPE=New Threshold(g)–Baseline Threshold(g)×100/15 grams– Baseline Threshold

According to this analysis, the higher the %MPE, the better the antinociceptive effect. As shown in FIGS. 8A and 8B, SNX-111, SNX-273 and SNX-279 each blocked mechanical allodynia significantly in comparison to saline control (asterisks in the figures indicate statistically significant differences between treatment and saline, $p<0.05$, Student's t test). The apparent order of potency for suppression of allodynia is SNX-111=SNX-273>SNX-279. This is consistent with the compounds' relative affinities at the SNX-111 binding site ($IC_{50}$'s: SNX-111, 8 pM; SNX-273, 8 pM; SNX-279, 40 pM).

Animals were also observed for the appearance of general motor dysfunction, as evidenced by inability to ambulate symmetrically and for any other overt signs of unusual activity. No effects on motor activity were observed in saline-treated animals; a dose-dependent tremor characteristic of SNX-111 administration was observed in animals given SNX-111.

EXAMPLE 5

Methionine-Lactate Buffer Formulations

Analgesic efficacy of spinally-administered SNX-111 was tested using a methionine-lactate buffer formulation in the paradigm detailed in Example 4. SNX-111 (10 µg/ml) and L-methionine (50 µg/ml) were dissolved in a vehicle comprised of sodium lactate (150 mM) adjusted to pH 4–4.5 with 250 mM lactic acid. This formulation was used to deliver 0.1 µg SNX-111 intrathecally, as described in Example 5 at 30, 60, 120 and 240 minutes after treatment with test or control compound. FIG. 9 shows effects on mechanical allodynia of a single intrathecal bolus injection of 10 µl saline (open circles) or lactate buffer (150 mM) containing 50 µg/ml methionine with (closed squares) or without (closed triangles) 10 µg/ml SNX-111. Neither saline alone or methionine lactate control buffer alone was effective to suppress allodynia, whereas the SNX-111 formulation was effective in this regard (FIG. 9). Moreover, it was observed that %MPE values for saline-treated controls were not significantly different from those of animals given methionine-lactate buffer alone.

Although the invention has been described with respect to particular embodiments, it will be apparent to those skilled that various changes and modifications can be made without departing from the invention.

It is claimed:

1. A stable omega conopeptide formulation comprising an omega conopeptide and an anti-oxidant composition capable of preventing methionine oxidation.

2. The formulation of claim 1, wherein the anti-oxidant composition includes a carboxylic acid buffer.

3. The formulation of claim 2, wherein the carboxylic acid buffer is lactate buffer.

4. The formulation of claim 1, wherein the anti-oxidant is methionine.

5. The formulation of claim 1, wherein the anti-oxidant composition includes lactate buffer and methionine.

6. An omega-conopeptide SNX-273 having the sequence: SEQ ID NO: 35.

7. An omega conopeptide SNX-279 having the sequence SEQ ID NO: 36.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: MVIIA/SNX- 111, FIGURE 1

( x i ) SEQUENCE DESCRIPTION: SEQ ID NO:1:

```
Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: MVIIB/SNX- 159, FIGURE 1

( x i ) SEQUENCE DESCRIPTION: SEQ ID NO:2:

```
Cys Lys Gly Lys Gly Ala Ser Cys His Arg Thr Ser Tyr Asp Cys Cys
1               5                   10                  15

Thr Gly Ser Cys Asn Arg Gly Lys Cys
            20                  25
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: GVIA/SNX- 124, FIGURE 1

( i x ) FEATURE:
        ( A ) NAME/KEY: Modified-site
        ( B ) LOCATION: 4
        ( D ) OTHER INFORMATION: /note= "where X is hydroxyproline"

( i x ) FEATURE:
        ( A ) NAME/KEY: Modified-site
        ( B ) LOCATION: 10
        ( D ) OTHER INFORMATION: /note= "where X is hydroxyproline"

( i x ) FEATURE:
        ( A ) NAME/KEY: Modified-site ( B ) LOCATION: 21
                    ( D ) OTHER INFORMATION: /note= "where X is hydroxyproline"

( x i ) SEQUENCE DESCRIPTION: SEQ ID NO:3:

Cys Lys Ser Xaa Gly Ser Ser Cys Ser Xaa Thr Ser Tyr Asn Cys Cys
 1               5                   10                  15

Arg Ser Cys Asn Xaa Tyr Thr Lys Arg Cys Tyr
                20                  25

( 2 ) INFORMATION FOR SEQ ID NO:4:

( i ) SEQUENCE CHARACTERISTICS:
                    ( A ) LENGTH: 29 amino acids
                    ( B ) TYPE: amino acid
                    ( D ) TOPOLOGY: linear ( i i ) MOLECULE TYPE: protein ( i i i ) HYPOTHETICAL: NO ( v i ) ORIGINAL SOURCE:
                    ( C ) INDIVIDUAL ISOLATE: GVIIA/SNX- 178, FIGURE 1

( i x ) FEATURE:
                    ( A ) NAME/KEY: Modified-site
                    ( B ) LOCATION: 4
                    ( D ) OTHER INFORMATION: /note= "where X is hydroxyproline"

( i x ) FEATURE:
                    ( A ) NAME/KEY: Modified-site
                    ( B ) LOCATION: 7
                    ( D ) OTHER INFORMATION: /note= "where X is hydroxyproline"

( x i ) SEQUENCE DESCRIPTION: SEQ ID NO:4:

Cys Lys Ser Xaa Gly Thr Xaa Cys Ser Arg Gly Met Arg Asp Cys Cys
 1               5                   10                  15

Thr Ser Cys Leu Leu Tyr Ser Asn Lys Cys Arg Arg Tyr
                20                  25

( 2 ) INFORMATION FOR SEQ ID NO:5:

( i ) SEQUENCE CHARACTERISTICS:
                    ( A ) LENGTH: 27 amino acids
                    ( B ) TYPE: amino acid
                    ( D ) TOPOLOGY: linear ( i i ) MOLECULE TYPE: protein ( i i i ) HYPOTHETICAL: NO ( v i ) ORIGINAL SOURCE:
                    ( C ) INDIVIDUAL ISOLATE: RVIA/SNX- 182, FIGURE 1

( i x ) FEATURE:
                    ( A ) NAME/KEY: Modified-site
                    ( B ) LOCATION: 4
                    ( D ) OTHER INFORMATION: /note= "where X is hydroxyproline"

( i x ) FEATURE:
                    ( A ) NAME/KEY: Modified-site
                    ( B ) LOCATION: 7
                    ( D ) OTHER INFORMATION: /note= "where X is hydroxyproline"

( x i ) SEQUENCE DESCRIPTION: SEQ ID NO:5:

Cys Lys Pro Xaa Gly Ser Xaa Cys Arg Val Ser Ser Tyr Asn Cys Cys
 1               5                   10                  15

Ser Ser Cys Lys Ser Tyr Asn Lys Lys Cys Gly
                20                  25

( 2 ) INFORMATION FOR SEQ ID NO:6:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: SVIA/SNX- 157, FIGURE 1

( i x ) FEATURE:
( A ) NAME/KEY: Modified-site
( B ) LOCATION: 7
( D ) OTHER INFORMATION: /note= "where X is hydroxyproline"

( x i ) SEQUENCE DESCRIPTION: SEQ ID NO:6:

Cys Arg Ser Ser Gly Ser Xaa Cys Gly Val Thr Ser Ile Cys Cys Gly
1 5 10 15

Arg Cys Tyr Arg Gly Lys Cys Thr
20

( 2 ) INFORMATION FOR SEQ ID NO:7:

( i ) SEQUENCE CHARACTERISTICS:
( A ) LENGTH: 27 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: TVIA/SNX- 185, FIGURE 1

( i x ) FEATURE:
( A ) NAME/KEY: Modified-site
( B ) LOCATION: 4
( D ) OTHER INFORMATION: /note= "where X is hydroxyproline"

( i x ) FEATURE:
( A ) NAME/KEY: Modified-site
( B ) LOCATION: 10
( D ) OTHER INFORMATION: /note= "where X is hydroxyproline"

( i x ) FEATURE:
( A ) NAME/KEY: Modified-site
( B ) LOCATION: 21
( D ) OTHER INFORMATION: /note= "where X is hydroxyproline"

( x i ) SEQUENCE DESCRIPTION: SEQ ID NO:7:

Cys Leu Ser Xaa Gly Ser Ser Cys Ser Xaa Thr Ser Tyr Asn Cys Cys
1 5 10 15

Arg Ser Cys Asn Xaa Tyr Ser Arg Lys Cys Arg
20 25

( 2 ) INFORMATION FOR SEQ ID NO:8:

( i ) SEQUENCE CHARACTERISTICS:
( A ) LENGTH: 26 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: SVIB/SNX- 183, FIGURE 1

( x i ) SEQUENCE DESCRIPTION: SEQ ID NO:8:

```
Cys  Lys  Leu  Lys  Gly  Gln  Ser  Cys  Arg  Lys  Thr  Ser  Tyr  Asp  Cys  Cys
1                   5                        10                       15

Ser  Gly  Ser  Cys  Gly  Arg  Ser  Gly  Lys  Cys
               20                       25
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-190, FIGURE 2

( x i ) SEQUENCE DESCRIPTION: SEQ ID NO:9:

```
Cys  Lys  Gly  Ala  Gly  Ala  Lys  Cys  Ser  Arg  Leu  Met  Tyr  Asp  Cys  Cys
1                   5                        10                       15

Thr  Gly  Ser  Cys  Arg  Ser  Gly  Lys  Cys
               20                       25
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-191, FIGURE 2

( x i ) SEQUENCE DESCRIPTION: SEQ ID NO:10:

```
Cys  Ala  Gly  Ala  Gly  Ala  Lys  Cys  Ser  Arg  Leu  Met  Tyr  Asp  Cys  Cys
1                   5                        10                       15

Thr  Gly  Ser  Cys  Arg  Ser  Gly  Lys  Cys
               20                       25
```

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-193, FIGURE 2

( x i ) SEQUENCE DESCRIPTION: SEQ ID NO:11:

```
Cys  Lys  Gly  Ala  Gly  Ala  Lys  Cys  Ser  Arg  Leu  Met  Tyr  Asp  Cys  Cys
1                   5                        10                       15

Thr  Gly  Ser  Cys  Arg  Ser  Gly  Lys  Cys  Gly
               20                       25
```

( 2 ) INFORMATION FOR SEQ ID NO:12:

( i ) SEQUENCE CHARACTERISTICS:
        ( A ) LENGTH: 25 amino acids ( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: SNX-194, FIGURE 2

( i x ) FEATURE:
( A ) NAME/KEY: Modified-site
( B ) LOCATION: 12
( D ) OTHER INFORMATION: /note= "where X is Nle"

( x i ) SEQUENCE DESCRIPTION: SEQ ID NO:12:

Cys Lys Gly Ala Gly Ala Lys Cys Ser Arg Leu Xaa Tyr Asp Cys Cys
1               5                   10                  15

Thr Gly Ser Cys Arg Ser Gly Lys Cys
            20                  25

( 2 ) INFORMATION FOR SEQ ID NO:13:

( i ) SEQUENCE CHARACTERISTICS:
( A ) LENGTH: 25 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: SNX-195, FIGURE 2

( x i ) SEQUENCE DESCRIPTION: SEQ ID NO:13:

Cys Lys Gly Ala Gly Ala Lys Cys Ser Arg Leu Xaa Tyr Asp Cys Cys
1               5                   10                  15

Thr Gly Ser Cys Arg Ser Gly Ala Cys
            20                  25

( 2 ) INFORMATION FOR SEQ ID NO:14:

( i ) SEQUENCE CHARACTERISTICS:
( A ) LENGTH: 27 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: SNX-196, FIGURE 2

( x i ) SEQUENCE DESCRIPTION: SEQ ID NO:14:

Asn Cys Lys Gly Ala Gly Ala Lys Cys Ser Arg Leu Xaa Tyr Asp Cys
1               5                   10                  15

Cys Thr Gly Ser Cys Arg Ser Gly Ala Cys Gly
            20                  25

( 2 ) INFORMATION FOR SEQ ID NO:15:

( i ) SEQUENCE CHARACTERISTICS:
( A ) LENGTH: 27 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
   ( C ) INDIVIDUAL ISOLATE: SNX-197, FIGURE 2

( x i ) SEQUENCE DESCRIPTION: SEQ ID NO:15:

| Asn | Ser | Cys | Lys | Gly | Ala | Gly | Ala | Lys | Cys | Ser | Arg | Leu | Xaa | Tyr | Asp |
|---|---|---|---|---|---|---|---|---|---|---|---|---|---|---|---|
| 1 | | | | 5 | | | | | 10 | | | | | 15 | |

| Cys | Cys | Thr | Gly | Ser | Cys | Arg | Ser | Gly | Ala | Cys |
|---|---|---|---|---|---|---|---|---|---|---|
| | | | 20 | | | | | 25 | | |

( 2 ) INFORMATION FOR SEQ ID NO:16:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-198, FIGURE 2

( x i ) SEQUENCE DESCRIPTION: SEQ ID NO:16:

| Cys | Lys | Gly | Lys | Gly | Ala | Lys | Cys | Ser | Arg | Leu | Met | Tyr | Asp | Cys | Cys |
|---|---|---|---|---|---|---|---|---|---|---|---|---|---|---|---|
| 1 | | | | 5 | | | | | 10 | | | | | 15 | |

| Thr | Gly | Ser | Cys | Ala | Ser | Gly | Lys | Cys |
|---|---|---|---|---|---|---|---|---|
| | | | 20 | | | | | 25 |

( 2 ) INFORMATION FOR SEQ ID NO:17:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-200, FIGURE 2

( x i ) SEQUENCE DESCRIPTION: SEQ ID NO:17:

| Cys | Lys | Gly | Ala | Gly | Ala | Ala | Cys | Ser | Arg | Leu | Met | Tyr | Asp | Cys | Cys |
|---|---|---|---|---|---|---|---|---|---|---|---|---|---|---|---|
| 1 | | | | 5 | | | | | 10 | | | | | 15 | |

| Thr | Gly | Ser | Cys | Arg | Ser | Gly | Lys | Cys |
|---|---|---|---|---|---|---|---|---|
| | | | 20 | | | | | 25 |

( 2 ) INFORMATION FOR SEQ ID NO:18:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-201, FIGURE 2

( x i ) SEQUENCE DESCRIPTION: SEQ ID NO:18:

| Cys | Lys | Gly | Lys | Gly | Ala | Lys | Cys | Arg | Lys | Thr | Ser | Tyr | Asp | Cys | Cys |
|---|---|---|---|---|---|---|---|---|---|---|---|---|---|---|---|
| 1 | | | | 5 | | | | | 10 | | | | | 15 | |

| Thr | Gly | Ser | Cys | Arg | Ser | Gly | Lys | Cys |
|---|---|---|---|---|---|---|---|---|
| | | | 20 | | | | | 25 |

( 2 ) INFORMATION FOR SEQ ID NO:19:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-202, FIGURE 2

( x i ) SEQUENCE DESCRIPTION: SEQ ID NO:19:

```
Cys Lys Leu Lys Gly Gln Ser Cys Ser Arg Leu Met Tyr Asp Cys Cys
1               5                   10                  15

Ser Gly Ser Cys Gly Arg Ser Gly Lys Cys
            20                  25
```

( 2 ) INFORMATION FOR SEQ ID NO:20:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-207, FIGURE 2

( i x ) FEATURE:
        ( A ) NAME/KEY: Modified-site
        ( B ) LOCATION: 4
        ( D ) OTHER INFORMATION: /note= "where X is hydroxyproline"

( i x ) FEATURE:
        ( A ) NAME/KEY: Modified-site
        ( B ) LOCATION: 21
        ( D ) OTHER INFORMATION: /note= "where X is hydroxyproline"

( x i ) SEQUENCE DESCRIPTION: SEQ ID NO:20:

```
Cys Leu Ser Xaa Gly Ser Ser Cys Ser Arg Leu Met Tyr Asn Cys Cys
1               5                   10                  15

Arg Ser Cys Asn Xaa Tyr Ser Arg Lys Cys Arg
            20                  25
```

( 2 ) INFORMATION FOR SEQ ID NO:21:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-231, FIGURE 2

( i x ) FEATURE:
        ( A ) NAME/KEY: Modified-site
        ( B ) LOCATION: 7
        ( D ) OTHER INFORMATION: /note= "where X is hydroxyproline"

( x i ) SEQUENCE DESCRIPTION: SEQ ID NO:21:

```
Cys Lys Gly Lys Gly Ala Xaa Cys Arg Lys Thr Met Tyr Asp Cys Cys
```

```
            1               5                    10                        15
         Ser  Gly  Ser  Cys  Gly  Arg  Arg  Gly  Lys  Cys
                        20                   25
```

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT ( x i ) SEQUENCE DESCRIPTION: SEQ ID NO:22:

```
Cys  Lys  Gly  Lys  Gly  Ala
1                   5
```

( 2 ) INFORMATION FOR SEQ ID NO:23:

( i ) SEQUENCE CHARACTERISTICS:
        ( A ) LENGTH: 1 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT ( x i ) SEQUENCE DESCRIPTION: SEQ ID NO:23:

```
Cys

1
```

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT ( x i ) SEQUENCE DESCRIPTION: SEQ ID NO:24:

```
Tyr  Asp  Cys  Cys  Thr  Gly  Ser  Cys
1                   5
```

( 2 ) INFORMATION FOR SEQ ID NO:25:

( i ) SEQUENCE CHARACTERISTICS:
        ( A ) LENGTH: 1 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT (x i) SEQUENCE DESCRIPTION: SEQ ID NO:25:

Arg
1

(2) INFORMATION FOR SEQ ID NO:26:

(i) SEQUENCE CHARACTERISTICS:
        (A) LENGTH: 3 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: CONOPEPTIDE GROUP 1 FRAGMENT (x i) SEQUENCE DESCRIPTION: SEQ ID NO:26:

Gly Lys Cys
1

(2) INFORMATION FOR SEQ ID NO:27:

(i) SEQUENCE CHARACTERISTICS:
        (A) LENGTH: 9 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: CONOPEPTIDE GROUP 2 FRAGMENT (ix) FEATURE:
        (A) NAME/KEY: Modified-site
        (B) LOCATION: 4
        (D) OTHER INFORMATION: /note= "where X is hydroxyproline"

(x i) SEQUENCE DESCRIPTION: SEQ ID NO:27:

Cys Leu Ser Xaa Gly Ser Ser Cys Ser
1               5

(2) INFORMATION FOR SEQ ID NO:28:

(i) SEQUENCE CHARACTERISTICS:
        (A) LENGTH: 8 amino acids
        (B) TYPE: amino acid
        (D) TOPOLOGY: linear (ii) MOLECULE TYPE: protein (iii) HYPOTHETICAL: NO (vi) ORIGINAL SOURCE:
        (C) INDIVIDUAL ISOLATE: CONOPEPTIDE GROUP 2 FRAGMENT (x i) SEQUENCE DESCRIPTION: SEQ ID NO:28:

Tyr Asn Cys Cys Arg Ser Cys Asn
1            5

(2) INFORMATION FOR SEQ ID NO:29:

(i) SEQUENCE CHARACTERISTICS:
        (A) LENGTH: 26 amino acids
        (B) TYPE: amino acid
        (D) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: SNX-230, FIGURE 1

( x i ) SEQUENCE DESCRIPTION: SEQ ID NO:29:

```
Cys Lys Gly Lys Gly Ala Pro Cys Arg Lys Thr Met Tyr Asp Cys Cys
1               5                   10                  15
Ser Gly Ser Cys Gly Arg Arg Gly Lys Cys
            20              25
```

( 2 ) INFORMATION FOR SEQ ID NO:30:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: SNX-236, FIGURE 2

( x i ) SEQUENCE DESCRIPTION: SEQ ID NO:30:

```
Cys Leu Ser Xaa Gly Ser Ser Cys Ser Arg Leu Met Tyr Asn Cys Cys
1               5                   10                  15
Arg Ser Cys Asn Pro Tyr Ser Arg Lys Cys Arg
            20              25
```

( 2 ) INFORMATION FOR SEQ ID NO:31:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: CONOPEPTIDE GROUP 2 FRAGMENT ( x i ) SEQUENCE DESCRIPTION: SEQ ID NO:31:

```
Tyr Ser Arg Lys Cys Arg
1               5
```

( 2 ) INFORMATION FOR SEQ ID NO:32:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: SNX-239, FIGURE 2

( x i ) SEQUENCE DESCRIPTION: SEQ ID NO:32:

```
Cys Lys Gly Lys Gly Ala Lys Cys Ser Leu Leu Met Tyr Asp Cys Cys
1               5                   10                  15
Thr Gly Ser Cys Arg Ser Gly Lys Cys
            20              25
```

( 2 ) INFORMATION FOR SEQ ID NO:33:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-199, FIGURE 2

( x i ) SEQUENCE DESCRIPTION: SEQ ID NO:33:

```
Cys Lys Gly Lys Gly Ala Lys Cys Ser Ala Leu Met Tyr Asp Cys Cys
1               5                   10                  15
Thr Gly Ser Cys Arg Ser Gly Lys Cys
            20              25
```

( 2 ) INFORMATION FOR SEQ ID NO:34:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX 240, FIGURE 2

( i x ) FEATURE:
        ( A ) NAME/KEY: Modified-site
        ( B ) LOCATION: 1
        ( D ) OTHER INFORMATION: /note= "The cysteine residue
            carries an acetyl group"

( x i ) SEQUENCE DESCRIPTION: SEQ ID NO:34:

```
Cys Lys Gly Lys Gly Ala Lys Cys Ser Leu Leu Met Tyr Asp Cys Cys
1               5                   10                  15
Thr Gly Ser Cys Arg Ser Gly Lys Cys
            20              25
```

( 2 ) INFORMATION FOR SEQ ID NO:35:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: SNX-273, FIGURE 2

( x i ) SEQUENCE DESCRIPTION: SEQ ID NO:35:

```
Cys Lys Gly Lys Gly Ala Lys Cys Ser Arg Leu Ala Tyr Asp Cys Cys
1               5                   10                  15
Thr Gly Ser Cys Arg Ser Gly Lys Cys
            20              25
```

( 2 ) INFORMATION FOR SEQ ID NO:36:

( i ) SEQUENCE CHARACTERISTICS:

-continued ( A ) LENGTH: 25 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( C ) INDIVIDUAL ISOLATE: SNX-279, FIGURE 2

( i x ) FEATURE:
( A ) NAME/KEY: Modified-site
( B ) LOCATION: 12
( D ) OTHER INFORMATION: /note= "where X is sulfoxy-methionine"

( x i ) SEQUENCE DESCRIPTION: SEQ ID NO:36:

```
Cys Lys Gly Lys Gly Ala Lys Cys Ser Arg Leu Xaa Tyr Asp Cys Cys
1               5                   10                  15

Thr Gly Ser Cys Arg Ser Gly Lys Cys
            20                  25
```